(12) United States Patent
Varmus et al.

(10) Patent No.: US 8,501,413 B2
(45) Date of Patent: *Aug. 6, 2013

(54) METHODS AND COMPOSITIONS FOR DETECTING A DRUG RESISTANT EGFR MUTANT

(75) Inventors: Harold Varmus, New York, NY (US); Katerina Politi, New York, NY (US); William Pao, New York, NY (US); Vincent Miller, New York, NY (US)

(73) Assignee: Memorial-Sloan Kettering Cancer Center, New York, NY (US)

( * ) Notice: Subject to any disclaimer, the term of this patent is extended or adjusted under 35 U.S.C. 154(b) by 37 days.

This patent is subject to a terminal disclaimer.

(21) Appl. No.: 13/275,161

(22) Filed: Oct. 17, 2011

(65) Prior Publication Data

US 2012/0077201 A1    Mar. 29, 2012

Related U.S. Application Data

(63) Continuation of application No. 11/815,985, filed as application No. PCT/US2006/005050 on Feb. 13, 2006, now Pat. No. 8,067,175.

(60) Provisional application No. 60/652,488, filed on Feb. 11, 2005.

(51) Int. Cl.
*C12Q 1/68* (2006.01)

(52) U.S. Cl.
USPC .......................................................... 435/6.12

(58) Field of Classification Search
None
See application file for complete search history.

(56) References Cited

U.S. PATENT DOCUMENTS

| 7,294,468 | B2 | 11/2007 | Bell et al. | |
| 8,067,175 | B2 * | 11/2011 | Varmus et al. | 435/6.12 |
| 2010/0009360 | A1 | 1/2010 | Rosell Costa et al. | |

FOREIGN PATENT DOCUMENTS

WO    2005/118876 A2    12/2005

OTHER PUBLICATIONS

Blencke et al. (2003) The J. of Biol. Chem. vol. 278 No. 17 pp. 15435-15440.*
Buck et al. (1999) Biotechniques 27:5 pp. 236.*
Khatua et al. (2003) Cancer Res: 63: 1865-1870.*
Neff et al. (2002) Trends in genetics vol. 18 No. 12 pp. 613-615.*
Paez et al. (2004) Science vol. 304 pp. 1497-1500.*
Paez et al (2004) Science vol. 304 pp. 1497-1500 supplement.*
Genbank accession NM_005228 downloaded on Sep. 21, 2012.*
Al-Ali, H. et al. "High Incidence of BCR-ABL kinase domain mutations and absence of mutations of the PDGFR and KIT activiation loops in CML patients with secondary resistance to imatinib" Hematol. J., 2004. pp. 55-60, vol. 5.

Beaulieu, M. et al. "A Novel Method for Molecular Haplotyping Combining a Improved AS-PCR Technique with Base Specific Cleavage of Nuckeic Acid Analyzed by Mass Spectrometry" [title of item unknown], 2003, p. 441, vol. 73, No. 5.
Bell, D. et al. "Epidermal Growth Factor Receptor Mutations and Gene Amplification in Non-Small-Cell Lung Cancer: Molecular Analysis of the IDEAL/INTACT Gefitinib Trials." Journal of Clinical Oncology, Nov. 2005, pp. 1-12, vol. 23, No. 31.
Blencke, S. et al. "Mutation of Threonine 766 in the Epidermal Growth Factor Receptor Reveals a Hotspot for Resistance Formation against Selective Tyrosine Kinase Inhibitors." The Journal of Biological Chemistry, 2003, pp. 15435-15440, vol. 278, No. 17.
Blencke, S. et al. "Characterization of a Conserved Structural Determinant Controlling Protein Kinase Sensitivity to Selective Inhibitors." Chemistry and Biology, May 2004, pp. 691-701, vol. 11.
Bozyczko-Coyne, D. et al. "A rapid fluorometric assay to measure neuronal survival in vitro" J. Neuroscience Meth., 1993, pp. 205-216, vol. 50.
Buck, G. et al. "Design Strategies and Performance of Custom DNA Sequencing Primers" BioTechniques, Sep. 1999, pp. 528-536, vol. 27.
Choi, Y. et al. "EML4-ALK Mutations in Lung Cancer that Confer Resistance to ALK Inhibitors." The New England Journal of Medicine, 2010, pp. 1734-1739.
Cools, J. et al. "A tyrosine kinase created by fusion of the PDGFRA and FIP1L1 genes as a therapeutic target of imatinib in idiopathic hypereosinophilic syndrome" New England Journal of Medicine, 2003, pp. 1201-1214, vol. 348.
Daub, H. et al. "Strategies to overcome resistance to targeted protein kinase inhibitors" Nat. Rev. Drug Discov., 2004, pp. 1001-1010, vol. 3.
Deininger, M et al. "The development of imatinib as a therapeutic agent for chronic myeloid leukemia" Blood, 2004, prepublished online DOI 10.1182/blood-2004-08-3097.
Eberhard, D. "Mutations in the Epidermal Growth Factor Receptor and in KRAS are Predictive and Prognostic Indicators in Patients with Non-Small-Cell Lung cancer Treated with Chemotherapy Alone and in Combination with Erlotinib." Journal of Clinical Oncology, 2005, pp. 1-14, vol. 23, No. 25.
Gatzemeier, U. et al. "Phase III Study of Erlotinib in Combination with Cisplatin and Gemcitabine in Advanced Non-Small-Cell Lung Cancer: The Tarceva Lung Cancer Investigation Trial." Journal of Clinical Oncology, Apr. 2007, pp. 1545-1552, vol. 25, No. 12.
Genebank Acession No. T39469.1 ya06c09.r1 Stratagene placenta (#937225) *Homo sapiens* cDNA Image:60688 5-similar to SP: EGFR_HUMAN P00533 Epidermal Growth Factor Receptor Precursor, m sequence, updated 1995, pp. 1-2, retrieved 2010.

(Continued)

*Primary Examiner* — Samuel Woolwine
*Assistant Examiner* — Suchira Pande
(74) *Attorney, Agent, or Firm* — Larson & Anderson, LLC

(57) ABSTRACT

Development of acquired resistance to the therapeutic effects of an epidermal growth factor (EGFR) tyrosine kinase inhibitor in a patient that is suffering from a cancer is predicted by:
(a) obtaining a sample from the patient, wherein the cancer harbors a somatic gain-of-function mutation in the tyrosine kinase domain of EGFR that enhances the sensitivity of the cancer to the tyrosine kinase inhibitor, and
(b) testing the sample to determine whether the gene encoding EGFR is present in a mutant form that encodes a T790M mutant of EGFR in addition to the somatic gain of function mutation. A finding that the mutant form is present indicates that the cancer has become or will become resistant to the EGFR tyrosine kinase inhibitor.

24 Claims, 11 Drawing Sheets

OTHER PUBLICATIONS

Godin-Heymann, N. et al. "The T790M "gatekeeper" mutation in EGFR mediates resistance to low concentrations of an irreversible EGFR inhibitor." Molecular Cancer Therapeutics., 2008, pp. 874-879, vol. 7, No. 4.

Gorre, M. et al. "Clinical resistance to STI-571 cancer therapy caused by BCR-ABL gene mutation or amplification" Science, 2001, pp. 876-880, vol. 293.

Gorre, M. et al "Molecular mechanisms of resistance to STI571 in chronic myeloid leukemia" Curr. Opin. Hematol, 2002, pp. 303-307, vol. 9.

Hirsch, F. et al. "Molecular Predictors of Outcome with Gefitinib in a Phase III Placebo-Controlled Study in Advanced Non-Small-Cell Lung Cancer." Journal of Clinical Oncology, Nov. 2006, pp. 5034-5042, vol. 24, No. 31.

Huang, S. et al. "High Frequency of epidermal growth factor receptor mutations with complex patterns in non-small cell lung cancers related to gefitinib responsiveness in Taiwan" Clin. Cancer Research, 2004, pp. 8195-8203, vol. 10.

Johannessen, C. et al. "COT drives resistance to RAF inhibition through MAP kinase pathway reactivation." Nature, 2010, pp. 1-5, vol. 000, Macmillan Publishers Limited.

Khatua, S. et al. "Overexpression of the EGFR/FKBP12/HIF-2α Pathway Identified in Childhood Astrocytomas by Angiogenesis Gene Profiling" Cancer Research, Apr. 15, 2003, pp. 1865-1870, vol. 63.

Kobayashi, S. et al. "EGFR Mutation and Resistance of Non-Small-Cell Lung Cancer to Gefitinib." The New England Journal of Medicine, 2005, pp. 786-792, vol. 352, No. 8.

Kopetz, S. et al. "PLX4032 in metastatic colorectal cancer patients with mutant BRAF tumors." J. Clin. Oncology, 2010; (supplemental abstract 3534).

Kim, E. et al. "Gefitinib versus docetaxel in previously treated non-small-cell lung cancer (INTEREST): a randomised phase III trial." The Lancet, Nov. 2008, pp. 1809-1818, vol. 372.

Kosaka, T. et al. "Mutations of the epidermal growth factor receptor gene in lung cancer: Biological and clinical implications" Cancer Research, 2004, pp. 8919-8923, vol. 64.

Kreuzer, K. et al. "Preexiatence and evolution of imatinib mesylate-resistant clones in chronic myelogenous leukemia detected by a PNA-based PCR clamping technique" Ann Hematol, 2003, pp. 284-289, vol. 82.

Krug, L. et al. "Randomized phase II trial of trastuzumab (tras) plus either weekly docetaxel (doc) or paclitaxel (pac) in previously untreated advanced non-small cell lung cancer (NSCLC)" Proc. Am Soc. Clin. Oncol., 2001, p. 1328 vol. 20.

Lynch, T. et al. "Activating mutations in the epidermal growth factor receptor underlying responsiveness of non-small-cell lung cancer to gefitinib" New Engl. J. Med., May 20, 2004, pp. 2129-2139, vol. 350, No. 21.

Marchetti, A. et al. "EGFR mutations in non-small-cell lung cancer: analysis of a large series of cases and development of a rapid and sensitive method for diagnostic screening with potential implications on pharmacologic treatment" J. Clin. Oncol., Feb. 1, 2005, pp. 857-865, vol. 23, No. 4.

Mitsudomi, T. "Gefitinib versus cisplatin plus docetaxel in patients with non-small cell lung cancer harbouring mutation of the epidermal growth factor receptor (WJTOG3405): an open label, randomised phase 3 trial." The Lancet Oncology, 2009, pp. 1-8.

Mok, T. et al. "Gefitinib or Carboplatin-Paclitaxel in Pulmonary Adenocarcinoma." The New England Journal of Medicine, 2009, pp. 1-11, vol. 361.

Natale, R. et al. "Quantitative gene expression in non-small cell lung cancer from paraffin-embedded tissue specimens: Predicting response to gefitinib, an EGFR kinase inhibitor" Proc. Am. Soc. Clin. Oncol, 2003, (Abstr 763), vol. 22.

Nazarian, R. et al. "Melanomas acquire resistance to B-RAF (V600E) inhibition by RTK or N-RAS upregulation." Nature, 2010, pp. 1-5, vol. 000, Macmillan Publishers Limited.

Neff, M. et al. "Web-based primer design for single nucleotide polymorphism analysis" TRENDS in Genetics, Dec. 2002, pp. 613-615, vol. 18, No. 12.

O'Hare, T. et al. "Inhibition of wild-type and mutant BCR-Abl by AP23464, a potent ATP-based oncogenic protein kinase inhibitor: Implications for CML" Blood, 2004, pp. 2532-2539, vol. 104

Paez, J. et al. "EGFR mutations in lung cancer: Correlation with clinical response to gefitinib therapy" Science, 2004, pp. 1497-1500, vol. 304.

Paez, J. et al. Supplementary Material "Clinical response to Gefitinib therapy EGFR Mutations in Lung Cancer: Correlation with Clinical Response to Gefitinib" Science, 2004, pp. 1497-1500, vol. 304.

Pao, W. et al. "EGF Receptor gene mutations are common in lung cancers from "never smokers" and are associated with sensitivity of tumors to gefitinib and erlotinib" PNAS, 2004, pp. 13306-13311, vol. 101.

Pao, W. et al. "KRAS mutations and primary resistance of lung adenocarcinomas to gefitinib or erlotinib" PLoS Medicine, 2005, p. e17, vol. 2.

Pao, W. et al. "Acquired Resistance of Lung Adenocarcinomas to Gefitnib of Erlotinib is Associated With a Second Mutation in the EGFR Kinase Domain." PLOS Medicine, Mar. 2005, pp. 0225-0235, vol. 2, No. 3.

Pao, W. et al. "Rational, biologically based treatment of EGFR-mutant non-small-cell lung cancer." Nature, Nov. 2010, pp. 760-774, vol. 10.

Pastinen, T. et al. "A system for specific, high-throughput genotyping by allele-specific primer extension on microarrays", Genome Research, Jul. 1, 2000, pp. 1031-1042, vol. 10, No. 7.

Rieger, T. et al. "Detection of Small Amounts of Mutated Mitochondrial DNA by Allele-Specific PCR (AS-PCR)" Methods in Molecular and Cellular Biology, Jan. 1, 1993, pp. 121-127, vol. 4.

Russom, A. et al. "Single nucleotide polymorphism analysis by allele-specific primer extension with real-time bioluminescence detection in a microfluidic device" J. Chromatog., Oct. 3, 2003, pp. 37-45, vol. 1014, No. 1-2.

Sawyer, C. "Targeted Cancer Therapy" Nature, 2004, pp. 294-297, vol. 432.

Sequist, L. et al. "Neratinib, an Irreversible Pan-ErbB Receptor Tyrosine Kinase Inhibitor: Results of a Phase II Trial in Patients with Advanced Non-Small-Cell Lung Cancer." Journal of Clinical Oncology, 2010, pp. 1-8.

Shah, N. et al. "Multiple BCR-ABL kinase domain mutations confer polyclonal resistance to the tyrosine kinase inhibitor imatinib (ST1571) in chronic phase and blast crisis chronic myeloid leukemia" Cancer Cell, 2002, pp. 117-125, vol. 2.

Shah, N. et al. "Overriding imatinib resistance with a novel ABL kinase inhibitor" Science, 2004, pp. 399-401, vol. 305.

Shigenatsu, H. et al. "Clinical and Biological features associated with epidermal growth factor receptor gene mutations in lung cancers" J. Natl. Cancer Inst., 2004, pp. 339-346, vol. 97.

Sordella, R. et al. "Gefitinib-sensitizing EGFR mutations in lung cancer activate anti-apoptotic pathways" Science, 2004, pp. 1163-1167, vol. 305.

Stamos, J. et al. "Structure of the epidermal growth factor receptor kinase domain alone and in complex with a 4-anilinoquinazoline inhibitor" J. Biol. Chem., 2002, pp. 46265-46272, vol. 277.

Tamborini, E. et al. "A new mutation in the KIT ATP pocket causes acquired resistance to imatinib in a gastrointestinal stromal tumor patient" Gastroenterology, 2004, pp. 294-299, vol. 127.

Tracy, S. et al. "Gefitinib induces apoptosis in the EGFRL858R non-small cell lung cancer cell line H3255" Cancer Research, 2004, pp. 7241-7244, vol. 64.

Ugozzoli, L. et al. "Detection of specific alleles by using allele-specific primer extension followed by capture on solid support" Genetic Anal.: Biomol. Eng., Aug. 1, 1992, pp. 107-112, vol. 9, No. 4.

Wagle, N. et al. "Dissecting Therapeutic Resistance to RAF Inhibition in Melanoma by Tumor Genomic Profiling." Journal of Clinical Oncology, 2011, pp. 1-12.

Whittaker, S. et al. "Gatekeeper Mutations Mediate Resistance to BRAF-Targeted Therapies." Cancer, Jun. 2010, pp. 1-10, vol. 2, No. 35.

Whittaker, Steven et al. "Gatekeeper Mutations Mediate Resistance to BRAF-Targeted Therapies" Supplementary Materials, Science Translational Medicine, Jun. 2010, pp. 1-6, vol. 2.

Wood, E. et al. "A unique structure for epidermal growth factor receptor bound to GW572016 (Lapatinib): Relationships amoung protein conformation, inhibitor off-rate, and receptor activity in tumor cells" Cancer Research, 2004, pp. 6652-6659, vol. 64.

Wu, D. et al. "Allele-Specific Enzymatic Amplification of Beta-Globin Genomic DNA for Diagnosis of Sickle Cell Anemia", PNAS, Apr. 1, 1989, pp. 2757-2760, vol. 86.

Zhu, Chang-Qi et al. "Role of KRAS and EGFR as Biomarkers of Response to Erlotinib in National Cancer Institute of Canada Clinical Trials Group Study BR.21." Journal of Clinical Oncology, Sep. 2008, pp. 4268-4275.

Chen, L. et al. "A missense mutation in KIT kinase domain 1 correlates with imatinib resistance in gastrointestinal stromal tumors" Cancer Research, Sep. 1, 2004, pp. 5913-5919, vol. 64.

* cited by examiner

Figure 1
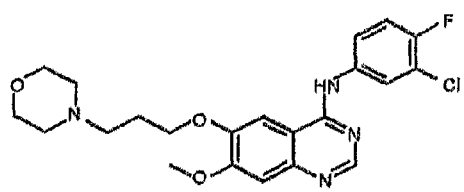
ZD1839; gefitinib
Iressa
AstraZeneca
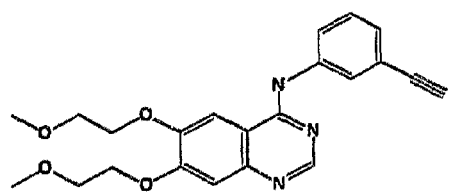
OSI-774; erlotinib
Tarceva
Genentech
Figure 2
a) 1 — SEQ — ≤ 200
b) 1 — FRAGMENT ≥ 11 — ≤ 200
c) 1 — SEQ — ≤ 200
d) 1 — COMPL — ≤ 200

CT-guided biopsy - lung

Pleural effusion

CT-guided biopsy - bone

Fluoroscopic-guided biopsy - lung

Case 3 – exon 20

H1975

SEQUENCE LISTING

<160> NUMBER OF SEQ ID NOS: 28

<210> SEQ ID NO 1
<211> LENGTH: 3633
<212> TYPE: DNA
<213> ORGANISM: Homo sapiens

<400> SEQUENCE: 1

| | | | | | |
|---|---|---|---|---|---|
| atgcgaccct | ccgggacggc | cggggcagcg | ctcctggcgc | tgctggctgc | gctctgcccg | 60 |
| gcgagtcggg | ctctggagga | aaagaaagtt | tgccaaggca | cgagtaacaa | gctcacgcag | 120 |
| ttgggcactt | ttgaagatca | ttttctcagc | ctccagagga | tgttcaataa | ctgtgaggtg | 180 |
| gtccttggga | atttgaaat | tacctatgtg | cagaggaatt | atgatctttc | cttcttaaag | 240 |
| accatccagg | aggtggctgg | ttatgtcctc | attgccctca | acacagtgga | gcgaattcct | 300 |
| ttggaaaacc | tgcagatcat | cagaggaaat | atgtactacg | aaaattccta | tgccttagca | 360 |
| gtcttatcta | actatgatgc | aaataaaacc | ggactgaagg | agctgcccat | gagaaattta | 420 |
| caggaaatcc | tgcatggcgc | cgtgcggttc | agcaacaacc | ctgccctgtg | caacgtggag | 480 |
| agcatccagt | ggcgggacat | agtcagcagt | gactttctca | gcaacatgtc | gatggacttc | 540 |
| cagaaccacc | tgggcagctg | ccaaaagtgt | gatccaagct | gtcccaatgg | agctgctgg | 600 |
| ggtgcaggag | aggagaactg | ccagaaactg | accaaaatca | tctgtgccca | gcagtgctcc | 660 |
| gggcgctgcc | gtggcaagtc | ccccagtgac | tgctgccaca | accagtgtgc | tgcaggctgc | 720 |
| acaggccccc | gggagagcga | ctgcctggtc | tgccgcaaat | tccgagacga | agccacgtgc | 780 |
| aaggacacct | gccccccact | catgctctac | aaccccacca | cgtaccagat | ggatgtgaac | 840 |
| cccgagggca | aatacagctt | tggtgccacc | tgcgtgaaga | agtgtccccg | taattatgtg | 900 |
| gtgacagatc | acggctcgtg | cgtccgagcc | tgtggggccg | acagctatga | gatggaggaa | 960 |
| gacggcgtcc | gcaagtgtaa | gaagtgcgaa | gggccttgcc | gcaaagtgtg | taacggaata | 1020 |
| ggtattggtg | aatttaaaga | ctcactctcc | ataaatgcta | cgaatattaa | acacttcaaa | 1080 |
| aactgcacct | ccatcagtgg | cgatctccac | atcctgccgg | tggcatttag | gggtgactcc | 1140 |
| ttcacacata | ctcctcctct | ggatccacag | gaactggata | ttctgaaaac | cgtaaaggaa | 1200 |
| atcacagggt | ttttgctgat | tcaggcttgg | cctgaaaaca | ggacggacct | ccatgccttt | 1260 |
| gagaacctag | aaatcatacg | cggcaggacc | aagcaacatg | gtcagttttc | tcttgcagtc | 1320 |
| gtcagcctga | acataacatc | cttgggatta | cgctccctca | aggagataag | tgatggagat | 1380 |
| gtgataattt | caggaaacaa | aaatttgtgc | tatgcaaata | caataaactg | gaaaaaactg | 1440 |
| tttgggacct | ccggtcagaa | aaccaaaatt | ataagcaaca | gaggtgaaaa | cagctgcaag | 1500 |
| gccacaggcc | aggtctgcca | tgccttgtgc | tcccccgagg | gctgctgggg | cccggagccc | 1560 |
| agggactgcg | tctcttgccg | gaatgtcagc | cgaggcaggg | aatgcgtgga | caagtgcaac | 1620 |
| cttctggagg | gtgagccaag | ggagtttgtg | gagaactctg | agtgcataca | gtgccaccca | 1680 |
| gagtgcctgc | ctcaggccat | gaacatcacc | tgcacaggac | ggggaccaga | caactgtatc | 1740 |
| cagtgtgccc | actacattga | cggcccccac | tgcgtcaaga | cctgcccggc | aggagtcatg | 1800 |
| ggagaaaaca | cacccctggt | ctggaagtac | gcagacgccg | ccatgtgtg | ccacctgtgc | 1860 |
| catccaaact | gcacctacgg | atgcactggg | ccaggtcttg | aaggctgtcc | aacgaatggg | 1920 |
| cctaagatcc | cgtccatcgc | cactgggatg | gtggggccc | tcctcttgct | gctggtggtg | 1980 |
| gccctgggga | tcggcctctt | catgcgaagg | cgccacatcg | ttcggaagcg | cacgctgcgg | 2040 |

-continued

```
aggctgctgc aggagaggga gcttgtggag cctcttacac ccagtggaga agctcccaac    2100
caagctctct tgaggatctt gaaggaaact gaattcaaaa agatcaaagt gctgggctcc    2160
ggtgcgttcg gcacggtgta taagggactc tggatcccag aaggtgagaa agttaaaatt    2220
cccgtcgcta tcaaggaatt aagagaagca acatctccga aagccaacaa ggaaatcctc    2280
gatgaagcct acgtgatggc cagcgtggac aacccccacg tgtgccgcct gctgggcatc    2340
tgcctcacct ccaccgtgca gctcatcatg cagctcatgc ccttcggctg cctcctggac    2400
tatgtccggg aacacaaaga caatattggc tcccagtacc tgctcaactg gtgtgtgcag    2460
atcgcaaagg gcatgaacta cttggaggac cgtcgcttgg tgcaccgcga cctggcagcc    2520
aggaacgtac tggtgaaaac accgcagcat gtcaagatca cagattttgg gctggccaaa    2580
ctgctgggtg cggaagagaa agaataccat gcagaaggag gcaaagtgcc tatcaagtgg    2640
atggcattgg aatcaatttt acacagaatc tatacccacc agagtgatgt ctggagctac    2700
ggggtgaccg tttgggagtt gatgacctt ggatccaagc catatgacgg aatccctgcc     2760
agcgagatct cctccatcct ggagaaagga gaacgcctcc ctcagccacc catatgtacc    2820
atcgatgtct acatgatcat ggtcaagtgc tggatgatag acgcagatag tcgcccaaag    2880
ttccgtgagt tgatcatcga attctccaaa atggcccgag accccagcg ctaccttgtc     2940
attcagggg atgaaagaat gcatttgcca agtcctacag actccaactt ctaccgtgcc     3000
ctgatggatg aagaagacat ggacgacgtg gtggatgccg acgagtacct catcccacag    3060
cagggcttct tcagcagccc ctccacgtca cggactcccc tcctgagctc tctgagtgca    3120
accagcaaca attccaccgt ggcttgcatt gatagaaatg ggctgcaaag ctgtcccatc    3180
aaggaagaca gcttcttgca gcgatacagc tcagacccca caggcgcctt gactgaggac    3240
agcatagacg acaccttcct cccagtgcct gaatacataa accagtccgt tcccaaaagg    3300
cccgctggct ctgtgcagaa tcctgtctat cacaatcagc ctctgaaccc cgcgcccagc    3360
agagacccac actaccagga cccccacagc actgcagtgg caaccccga gtatctcaac     3420
actgtccagc ccacctgtgt caacagcaca ttcgacagcc ctgcccactg ggcccagaaa    3480
ggcagccacc aaattagcct ggacaaccct gactaccagc aggacttctt tcccaaggaa    3540
gccaagccaa atggcatctt taagggctcc acagctgaaa atgcagaata cctaagggtc    3600
gcgccacaaa gcagtgaatt tattggagca tga                                 3633
```

<210> SEQ ID NO 2
<211> LENGTH: 1204
<212> TYPE: PRT
<213> ORGANISM: Homo sapiens

<400> SEQUENCE: 2

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
        50                  55                  60

Leu Glu Ile Thr Tyr Val Gln Arg Asn Tyr Asp Leu Ser Phe Leu Lys
    65                  70                  75                  80

Thr Ile Gln Glu Val Ala Gly Tyr Val Leu Ile Ala Leu Asn Thr Val
                85                  90                  95
```

```
Glu Arg Ile Pro Leu Glu Asn Leu Gln Ile Ile Arg Gly Asn Met Tyr
            100                 105                 110
Tyr Glu Asn Ser Tyr Ala Leu Ala Val Leu Ser Asn Tyr Asp Ala Asn
            115                 120                 125
Lys Thr Gly Leu Lys Glu Leu Pro Met Arg Asn Leu Gln Glu Ile Leu
        130                 135                 140
His Gly Ala Val Arg Phe Ser Asn Asn Pro Ala Leu Cys Asn Val Glu
145                 150                 155                 160
Ser Ile Gln Trp Arg Asp Ile Val Ser Ser Asp Phe Leu Ser Asn Met
                    165                 170                 175
Ser Met Asp Phe Gln Asn His Leu Gly Ser Cys Gln Lys Cys Asp Pro
            180                 185                 190
Ser Cys Pro Asn Gly Ser Cys Trp Gly Ala Gly Glu Glu Asn Cys Gln
        195                 200                 205
Lys Leu Thr Lys Ile Ile Cys Ala Gln Gln Cys Ser Gly Arg Cys Arg
210                 215                 220
Gly Lys Ser Pro Ser Asp Cys Cys His Asn Gln Cys Ala Ala Gly Cys
225                 230                 235                 240
Thr Gly Pro Arg Glu Ser Asp Cys Leu Val Cys Arg Lys Phe Arg Asp
                    245                 250                 255
Glu Ala Thr Cys Lys Asp Thr Cys Pro Pro Leu Met Leu Tyr Asn Pro
            260                 265                 270
Thr Thr Tyr Gln Met Asp Val Asn Pro Glu Gly Lys Tyr Ser Phe Gly
        275                 280                 285
Ala Thr Cys Val Lys Lys Cys Pro Arg Asn Tyr Val Val Thr Asp His
        290                 295                 300
Gly Ser Cys Val Arg Ala Cys Gly Ala Asp Ser Tyr Glu Met Glu Glu
305                 310                 315                 320
Asp Gly Val Arg Lys Cys Lys Lys Cys Glu Gly Pro Cys Arg Lys Val
                    325                 330                 335
Cys Asn Gly Ile Gly Ile Gly Glu Phe Lys Asp Ser Leu Ser Ile Asn
            340                 345                 350
Ala Thr Asn Ile Lys His Phe Lys Asn Cys Thr Ser Ile Ser Gly Asp
        355                 360                 365
Leu His Ile Leu Pro Val Ala Phe Arg Gly Asp Ser Phe Thr His Thr
    370                 375                 380
Pro Pro Leu Asp Pro Gln Glu Leu Asp Ile Leu Lys Thr Val Lys Glu
385                 390                 395                 400
Ile Thr Gly Phe Leu Leu Ile Gln Ala Trp Pro Glu Asn Arg Thr Asp
                    405                 410                 415
Leu His Ala Phe Glu Asn Leu Glu Ile Ile Arg Gly Arg Thr Lys Gln
            420                 425                 430
His Gly Gln Phe Ser Leu Ala Val Val Ser Leu Asn Ile Thr Ser Leu
        435                 440                 445
Gly Leu Arg Ser Leu Lys Glu Ile Ser Asp Gly Asp Val Ile Ile Ser
    450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
                    485                 490                 495
Asn Ser Cys Lys Ala Thr Gly Gln Val Cys His Ala Leu Cys Ser Pro
            500                 505                 510
Glu Gly Cys Trp Gly Pro Glu Pro Arg Asp Cys Val Ser Cys Arg Asn
        515                 520                 525
```

```
Val Ser Arg Gly Arg Glu Cys Val Asp Lys Cys Lys Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Met Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
```

| | | | |
|---|---|---|---|
| 945 | 950 | 955 | 960 |

Phe Arg Glu Leu Ile Ile Glu Phe Ser Lys Met Ala Arg Asp Pro Gln
                        965                        970                       975

Arg Tyr Leu Val Ile Gln Gly Asp Glu Arg Met His Leu Pro Ser Pro
                        980                        985                       990

Thr Asp Ser Asn Phe Tyr Arg Ala Leu Met Asp Glu Asp Met Asp
                        995                        1000                   1005

Asp Val Val Asp Ala Asp Glu Tyr Leu Ile Pro Gln Gln Gly Phe Phe
    1010                     1015                    1020

Ser Ser Pro Ser Thr Ser Arg Thr Pro Leu Leu Ser Ser Leu Ser Ala
1025                   1030                   1035                   1040

Thr Ser Asn Asn Ser Thr Val Ala Cys Ile Asp Arg Asn Gly Leu Gln
                        1045                      1050                    1055

Ser Cys Pro Ile Lys Glu Asp Ser Phe Leu Gln Arg Tyr Ser Ser Asp
                        1060                      1065                    1070

Pro Thr Gly Ala Leu Thr Glu Asp Ser Ile Asp Asp Thr Phe Leu Pro
                        1075                      1080                    1085

Val Pro Glu Tyr Ile Asn Gln Ser Val Pro Lys Arg Pro Ala Gly Ser
    1090                     1095                    1100

Val Gln Asn Pro Val Tyr His Asn Gln Pro Leu Asn Pro Ala Pro Ser
1105                   1110                   1115                   1120

Arg Asp Pro His Tyr Gln Asp Pro His Ser Thr Ala Val Gly Asn Pro
                        1125                      1130                    1135

Glu Tyr Leu Asn Thr Val Gln Pro Thr Cys Val Asn Ser Thr Phe Asp
                        1140                      1145                    1150

Ser Pro Ala His Trp Ala Gln Lys Gly Ser His Gln Ile Ser Leu Asp
                        1155                      1160                    1165

Asn Pro Asp Tyr Gln Gln Asp Phe Phe Pro Lys Glu Ala Lys Pro Asn
    1170                     1175                    1180

Gly Ile Phe Lys Gly Ser Thr Ala Glu Asn Ala Glu Tyr Leu Arg Val
1185                   1190                   1195                   1200

Ala Pro Gln Ser

<210> SEQ ID NO 3
<211> LENGTH: 2160
<212> TYPE: DNA
<213> ORGANISM: Homo sapiens
<220> FEATURE:
<221> NAME/KEY: gene
<222> LOCATION: (161101)...(163260)

<400> SEQUENCE: 3

| | | | | |
|---|---|---|---|---|
| tttagcttcc | tcagcccaag | aatagcagaa | gggttaaaat | aaagtctgta tttatggctc | 60 |
| tgtcaaagga | aggcccctgc | cttggcagcc | agccggaatt | agcagggcag cagatgcctg | 120 |
| actcagtgca | gcatggattt | cccataggga | gcctggggc | acagcacaga gagaccactt | 180 |
| ctctttagaa | atgggtcccg | ggcagccagg | cagcctttag | tcactgtaga ttgaatgctc | 240 |
| tgtccatttc | aaaacctggg | actggtctat | tgaaagagct | tatccagcta ctctttgcag | 300 |
| aggtgctgtg | ggcagggtcc | ccagcccaaa | tgcccaccca | tttcccagag cacagtcagg | 360 |
| gccaagcctg | gcctgtgggg | aagggaggcc | tttctccctg | ctggctcggt gctcccggga | 420 |
| tgccttctcc | atcgcttgtc | ctctgcagca | cccacagcca | gcgttcctga tgtgcagggt | 480 |
| cagtcattac | ccagggtgtt | ccggacccca | cacagattcc | tacaggccct catgatattt | 540 |
| taaaacacag | catcctcaac | cttgaggcgg | aggtcttcat | aacaaagata ctatcagttc | 600 |

```
ccaaactcag agatcaggtg actccgactc ctcctttatc caatgtgctc ctcatggcca    660
ctgttgcctg ggcctctctg tcatggggaa tccccagatg cacccaggag gggccctctc    720
ccactgcatc tgtcacttca cagccctgcg taaacgtccc tgtgctaggt cttttgcagg    780
cacagctttt cctccatgag tacgtatttt gaaactcaag atcgcattca tgcgtcttca    840
cctggaaggg gtccatgtgc ccctccttct ggccaccatg cgaagccaca ctgacgtgcc    900
tctccctccc tccaggaagc ctacgtgatg ccagcgtgg acaaccccca cgtgtgccgc     960
ctgctgggca tctgcctcac ctccaccgtg cagctcatca cgcagctcat gcccttcggc   1020
tgcctcctgg actatgtccg ggaacacaaa gacaatattg ctcccagta cctgctcaac   1080 tggtgtgtgc agatcgcaaa ggtaatcagg gaagggagat acggggaggg gagataagga   1140
gccaggatcc tcacatgcgg tctgcgctcc tgggatagca agagtttgcc atggggatat   1200
gtgtgtgcgt gcatgcagca cacacacatt cctttatttt ggattcaatc aagttgatct   1260
tcttgtgcac aaatcagtgc ctgtcccatc tgcatgtgga aactctcatc aatcagctac   1320 cttttgaagaa ttttctcttt attgagtgct cagtgtggtc tgatgtctct gttcttattt   1380
ctctggaatt ctttgtgaat actgtggtga tttgtagtgg agaaggaata ttgcttcccc   1440
cattcaggac ttgataacaa ggtaagcaag ccaggccaag gccaggagga cccaggtgat   1500
agtggtggag tggagcaggt gccttgcagg aggcccagtg aggaggtgca aggagctgac   1560
agagggcgca gctgctgctg ctatgtggct ggggccttgg ctaagtgtcc ccctttccac   1620
aggctcgctc cagagccagg gcggggctga gagagcagag tggtcaggta gccctgcctg   1680
ggtgctggag acaggcacag aacaacaagc caggtatttc acagctggtg cggacccaga   1740
aagacttctg cttttgcccc aaaccccctcc catctccatc ccagtcttgc atcagttatt   1800
tgcactcaac ttgctaagtc ctatttttt ctaacaatgg gtatacattt catcccattg    1860
actttaaagg atttgcaggc aggccctgtc tctgagaata cgccgttgcc cgtcatctct   1920
ctccgacagc agggcagggg gtccagagat gtgccaggga ccagagggag ggagcagaca   1980
cccacccggc ctgggcaggt cctcctcatt gcttgcatcc gcctggttag cagtggcagt   2040
cagtcctgcc gagtcattcg tgaggcgctc acccaactcc aggcagatgt aaaaggtgac   2100
ctacaagaag acaaacaaaa acatctggag cgctcttatg ccagcatctg cccttgacac   2160
```

<210> SEQ ID NO 4
<211> LENGTH: 24
<212> TYPE: DNA
<213> ORGANISM: Homo sapiens

<400> SEQUENCE: 4
ctccctccag gaagcctacg tgat                                              24

<210> SEQ ID NO 5
<211> LENGTH: 20
<212> TYPE: DNA
<213> ORGANISM: Homo sapiens

<400> SEQUENCE: 5
tttgcgatct gcacacacca                                                   20

<210> SEQ ID NO 6
<211> LENGTH: 20
<212> TYPE: DNA
<213> ORGANISM: Homo sapiens

<400> SEQUENCE: 6

-continued

```
cccaaccaag ctctcttgag                                              20

<210> SEQ ID NO 7
<211> LENGTH: 21
<212> TYPE: DNA
<213> ORGANISM: Homo sapiens

<400> SEQUENCE: 7
atgacaaggt agcgctgggg g                                            21

<210> SEQ ID NO 8
<211> LENGTH: 50
<212> TYPE: DNA
<213> ORGANISM: Artificial Sequence
<220> FEATURE:
<223> OTHER INFORMATION: primer

<400> SEQUENCE: 8
taaaattccc gtcgctatca aggagccaac atctccgaaa gccaacaagg             50

<210> SEQ ID NO 9
<211> LENGTH: 50
<212> TYPE: DNA
<213> ORGANISM: Artificial Sequence
<220> FEATURE:
<223> OTHER INFORMATION: primer

<400> SEQUENCE: 9
ccttgttggc tttcggagat gttggctcct tgatagcgac gggaatttta             50

<210> SEQ ID NO 10
<211> LENGTH: 19
<212> TYPE: DNA
<213> ORGANISM: Artificial Sequence
<220> FEATURE:
<223> OTHER INFORMATION: primer

<400> SEQUENCE: 10
agctcatcat gcagctcat                                               19

<210> SEQ ID NO 11
<211> LENGTH: 19
<212> TYPE: DNA
<213> ORGANISM: Artificial Sequence
<220> FEATURE:
<223> OTHER INFORMATION: primer

<400> SEQUENCE: 11
atgagctgca tgatgagct                                               19

<210> SEQ ID NO 12
<211> LENGTH: 18
<212> TYPE: DNA
<213> ORGANISM: Artificial Sequence
<220> FEATURE:
<223> OTHER INFORMATION: primer

<400> SEQUENCE: 12
caccgtgcag ctcatcat                                                18

<210> SEQ ID NO 13
<211> LENGTH: 18
<212> TYPE: DNA
<213> ORGANISM: Artificial Sequence
<220> FEATURE:
<223> OTHER INFORMATION: primer
```

-continued

```
<400> SEQUENCE: 13
cgaagggcat gagctgcg                                                     18

<210> SEQ ID NO 14
<211> LENGTH: 18
<212> TYPE: DNA
<213> ORGANISM: Homo sapiens

<400> SEQUENCE: 14
caccgtgcag ctcatcac                                                     18

<210> SEQ ID NO 15
<211> LENGTH: 18
<212> TYPE: DNA
<213> ORGANISM: Homo sapiens

<400> SEQUENCE: 15
cgaagggcat gagctgca                                                     18

<210> SEQ ID NO 16
<211> LENGTH: 18
<212> TYPE: DNA
<213> ORGANISM: Homo sapiens

<400> SEQUENCE: 16
atcaaggaat taagagaa                                                     18

<210> SEQ ID NO 17
<211> LENGTH: 18
<212> TYPE: DNA
<213> ORGANISM: Homo sapiens

<400> SEQUENCE: 17
agatgttgct tctcttaa                                                     18

<210> SEQ ID NO 18
<211> LENGTH: 18
<212> TYPE: DNA
<213> ORGANISM: Homo sapiens
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 18
atcaaggaat taananaa                                                     18

<210> SEQ ID NO 19
<211> LENGTH: 15
<212> TYPE: DNA
<213> ORGANISM: Homo sapiens

<400> SEQUENCE: 19
caactcatca cgcag                                                        15

<210> SEQ ID NO 20
<211> LENGTH: 15
<212> TYPE: DNA
<213> ORGANISM: Homo sapiens

<400> SEQUENCE: 20
```
ctgcgtgatg agttg                                                                15

<210> SEQ ID NO 21
<211> LENGTH: 15
<212> TYPE: DNA
<213> ORGANISM: Homo sapiens

<400> SEQUENCE: 21
caactcatca tgcag                                                                15

<210> SEQ ID NO 22
<211> LENGTH: 15
<212> TYPE: DNA
<213> ORGANISM: Homo sapiens

<400> SEQUENCE: 22
ctgcatgatg agttg                                                                15

<210> SEQ ID NO 23
<211> LENGTH: 15
<212> TYPE: DNA
<213> ORGANISM: Homo sapiens
<220> FEATURE:
<221> NAME/KEY: misc_feature
<222> LOCATION: (13)..(13)
<223> OTHER INFORMATION: n is a, c, g, or t

<400> SEQUENCE: 23
ctgcgtgatg agntg                                                                15

<210> SEQ ID NO 24
<211> LENGTH: 15
<212> TYPE: DNA
<213> ORGANISM: Homo sapiens
<220> FEATURE:
<221> NAME/KEY: misc_feature
<222> LOCATION: (3)..(3)
<223> OTHER INFORMATION: n is a, c, g, or t

<400> SEQUENCE: 24
canctcatca cgcag                                                                15

<210> SEQ ID NO 25
<211> LENGTH: 15
<212> TYPE: DNA
<213> ORGANISM: Homo sapiens

<400> SEQUENCE: 25
ctgcgtgatg agctg                                                                15

<210> SEQ ID NO 26
<211> LENGTH: 15
<212> TYPE: DNA
<213> ORGANISM: Homo sapiens

<400> SEQUENCE: 26
caactcatca tgcag                                                                15

<210> SEQ ID NO 27
<211> LENGTH: 15
<212> TYPE: DNA
<213> ORGANISM: Homo sapiens

<400> SEQUENCE: 27
ctgcatgatg agttg                                                                15

```
<210> SEQ ID NO 28
<211> LENGTH: 299
<212> TYPE: DNA
<213> ORGANISM: Homo sapiens

<400> SEQUENCE: 28
gtattttgaa actcaagatc gcattcatgc gtcttcacct ggaaggggtc catgtgcccc        60
tccttctggc caccatgcga agccacactg acgtgcctct ccctccctcc aggaagccta      120
cgtgatggcc agcgtggaca accccacgt gtgccgcctg ctgggcatct gcctcacctc       180
caccgtgcag ctcatcacgc agctcatgcc cttcggctgc ctcctggact atgtccggga      240
acacaaagac aatattggct cccagtacct gctcaactgg tgtgtgcaga tcgcaaagg      299
```

US 8,501,413 B2

METHODS AND COMPOSITIONS FOR DETECTING A DRUG RESISTANT EGFR MUTANT

FIELD OF THE INVENTION

This invention relates to a method for testing for a mutation in the epidermal growth factor receptor (EGFR) gene or EGFR protein, such mutation being the underlying reason for resistance to certain cancer therapies directed towards inhibiting EGFR. This invention further relates to methods for developing new therapies that inhibit said mutant EGFR.

BACKGROUND OF THE INVENTION

The epidermal growth factor receptor (EGFR) has been identified as a relevant target for treatment of solid tumors, as it is involved in regulating cellular functions important in the proliferation and survival of cancer cells. EGFR is commonly expressed in a range of tumors, and high expression is often related to poor prognosis. A new class of targeted therapies directed at inhibiting the EGFR, tyrosine kinase inhibitors, have appeared. Two known examples are gefitinib (Iressa) or erlotinib (Tarceva). Despite initial responses of some patients to these therapies, patients eventually progress by unknown mechanisms of "acquired" resistance.

EGFR has been thought to play an important role in lung cancer. However only a small portion non-small cell lung cancers (NSCLCs) respond to Iressa or Tarceva (see FIG. 1 for structures). Lung adenocarcinomas from patients who respond to the tyrosine kinase inhibitors gefitinib or erlotinib usually harbor somatic gain-of-function mutations in exons encoding the tyrosine kinase domain of EGFR. Such mutations are found in about 10% of NSCLCs from the United States [1,2,3], with higher incidences observed in east Asia [2,4,5,6]. Some 90% of NSCLC-associated mutations occur as either multi-nucleotide in-frame deletions in exon 19, involving elimination of four amino acids, Leu-Arg-Glu-Ala, or as a single nucleotide substitution at nucleotide 2573 (T→G) in exon 21, resulting in substitution of arginine for leucine at position 858 (L858R). Both of these mutations are associated with sensitivity to the small-molecule kinase inhibitors gefitinib or erlotinib[1,2,3]. Unfortunately, nearly all patients who experience marked improvement on these drugs eventually develop progression of disease. While KRAS (v-Ki-ras2, Kirsten rat sarcoma viral oncogene homolog, a RAS family member) mutations have been associated with some cases of primary resistance to gefitinib or erlotinib [7], mechanisms underlying "acquired" or "secondary" resistance are unknown.

Therefore there is a need in the art for the determining the underlying causes of such resistance so that a diagnostic test can be developed and a more effective treatment provided. Moreover, there is a need in the art for new compounds that are able to treat patients that show cancer progression or relapse despite initial response to current EGFR inhibitors.

SUMMARY OF THE INVENTION

The present invention provides polymerase chain reaction primers directed to detecting the EGFR mutant C→T at the position corresponding to base 2369 of EGFR cDNA. This mutation encodes a change in the EGFR protein from threonine in the wild type to methionine in the mutant at position 790. This mutation is shown to be sparse in patients before or in early stages of treatment with gefitinib or erlotinib. But since the mutation abrogates sensitivity to these agents, cancer cells harboring the mutation are positively selected, leading to patients that are refractory to further treatment. The invention further provides methods to detect the mutation in patients, whose ultimate objective is early identification of refractory cases so that alternative treatments can be initiated.

In a first aspect the invention provides a PCR primer that hybridizes under suitable PCR conditions to a sense strand or to an antisense strand of a polynucleotide sequence 5' in each respective strand to a mutation of an EGFR gene that encodes a substitution of threonine by methionine at position 790 of the EGFR polypeptide, wherein the PCR primer binds within 200 nucleotides of said mutation. General primer structures are provided based on SEQ ID NOS:4-7 and 12-15 that may be larger or smaller than these particular sequences, as well as primers whose sequences may have a certain number of bases in the sequences given by SEQ ID NOS:4-7 and 12-15 that are substituted by other bases.

In another aspect the invention provides a PCR primer that hybridizes under suitable PCR conditions to a first polynucleotide encoding a wild type EGFR polypeptide, or a polynucleotide fragment thereof, wherein the primer hybridizes to the sense strand sequence or to the antisense strand sequence that includes the wild type C at the position corresponding to base 2369 of EGFR cDNA and wherein the primer hybridizes weakly or not at all to a second EGFR polynucleotide containing a mutant T at position 2369 under the PCR conditions.

In still a further embodiment the invention provides a PCR primer that hybridizes under suitable PCR conditions to a first polynucleotide encoding a mutant EGFR polypeptide, or a polynucleotide fragment thereof, wherein the primer hybridizes to the sense strand sequence or to the antisense strand sequence that includes a mutant T at the position corresponding to base 2369 of EGFR cDNA and wherein the primer hybridizes weakly or not at all to a second EGFR polynucleotide containing a wild type C at position 2369 under the PCR conditions. General primer structures are provided based on SEQ ID NOS:12 and 13 that may be larger or smaller than these particular sequences, as well as primers whose sequences may have a certain number of bases in the sequences given by SEQ ID NOS:12 and 13 that are substituted by other bases.

In still an additional aspect the invention provides a method of detecting a mutant epidermal growth factor receptor (EGFR) gene in a sample that includes probing the sample with a means for selectively detecting a nucleotide sequence containing a mutant T at the position corresponding to base 2369 of EGFR cDNA, and identifying that the base at said position is T. In a significant embodiment the means distinguishes between detecting a mutant T and a wild type C at said position.

In common embodiments the sample includes tissue or cells that are or are suspected of being cancerous or malignant. Such samples originate in a subject having or suspected of having a cancer or malignant tumor, and may be obtained by biopsy or similar surgical procedures.

In certain prevalent embodiments of this method the probing includes steps of
  a) if necessary, treating the sample to liberate the nucleic acids contained therein;
  b) contacting the nucleic acids obtained from the sample with a composition that includes a first PCR primer that hybridizes to the sense strand sequence or to the antisense strand sequence that includes the mutant T at the position corresponding to base 2369 of EGFR cDNA and wherein the primer hybridizes weakly or not at all to a second EGFR polynucleotide containing a wild type C at position 2369 under the PCR conditions; and c) carrying out a PCR reaction in the presence of a second PCR primer to provide a PCR amplicon containing a mutant T at the position corresponding to base 2369.

The PCR reaction may advantageously incorporate a label into the PCR amplicon; this permits the identifying step to include detecting the label.

In alternative frequent embodiments of this method the probing includes steps of
- a) if necessary, treating the sample to liberate the nucleic acids contained therein;
- b) contacting the nucleic acids obtained from the sample with a composition that includes a pair of polymerase chain reaction (PCR) primers that hybridize under suitable PCR conditions to a polynucleotide encoding an EGFR polypeptide wherein the pair of primers brackets the position corresponding to base 2369 of EGFR cDNA to provide a PCR mixture;
- c) carrying out a PCR reaction on the mixture to provide a PCR amplicon containing the position corresponding to base 2369; and
- d) contacting the amplicon with a cleaving means that cleaves the amplicon either
  - i) by cleaving an amplicon having a mutant T at the position corresponding to base 2369 within 6 bases of the position but not so cleaving an amplicon having a wild type C at the position, or
  - ii) by cleaving an amplicon having a wild type C at the position corresponding to base 2369 within 6 bases of the position but not so cleaving an amplicon having a mutant T at the position.

The PCR reaction may advantageously incorporate a label into the PCR amplicon thus permitting the identifying to include detecting a length polymorphisms of the cleaved labeled polynucleotides.

In still further common embodiments of this method the probing includes steps of
- a) if necessary, treating the sample to liberate the nucleic acids contained therein;
- b) immobilizing at least a portion of the nucleic acids obtained from the sample on a solid support; and
- c) contacting the immobilized nucleic acids with a probe oligonucleotide that hybridizes to a polynucleotide encoding an EGFR polypeptide wherein the sequence of the probe includes a base complementary to a mutant T at the position corresponding to base 2369 of EGFR cDNA and wherein the probe hybridizes weakly or not at all to a polynucleotide containing a wild type C at position 2369 under suitable hybridization conditions.

In a common embodiment of a method inverse to that just described the probing includes steps of
- a) if necessary, treating the sample to liberate the nucleic acids contained therein;
- b) immobilizing a probe oligonucleotide that hybridizes to a polynucleotide encoding an EGFR polypeptide wherein the sequence of the probe includes a base complementary to a mutant T at the position corresponding to base 2369 of EGFR cDNA and wherein the probe hybridizes weakly or not at all to a polynucleotide containing a wild type C at position 2369 on a solid support; and
- c) contacting the immobilized probe with at least a portion of the nucleic acids obtained from the sample under suitable hybridization conditions.

In these embodiments involving a solid support the component that binds to the immobilized partner includes a label and the identifying includes detecting the label.

In yet another aspect the invention provides a method of predicting resistance to the therapeutic effects of gefitinib or erlotinib in a subject suffering from or suspected of having a cancer. This method employs the steps described in the method of detecting a mutant epidermal growth factor receptor (EGFR) gene in a sample described in the preceding paragraphs, and concludes that upon a positive finding of a mutant at position 2369 the subject is predicted to be resistant to treatment by gefitinib or erlotinib.

In a further aspect the invention provides a kit that includes at least one container and, contained therein, a composition that includes at least one PCR primer described in the preceding paragraphs. In certain embodiments the kit further includes a cleaving means that cleaves an EGFR polynucleotide either
- a) by cleaving a polynucleotide having a mutant T at the position corresponding to base 2369 of EGFR cDNA within 6 bases of the position but not so cleaving a polynucleotide having a wild type C at the position, or
- b) by cleaving a polynucleotide having a wild type C at the position corresponding to base 2369 of EGFR cDNA within 6 bases of the position but not so cleaving a polynucleotide having a mutant T at the position.

BRIEF DESCRIPTION OF THE DRAWINGS

FIG. 1. Chemical structures of gefitinib and erlotinib.

FIG. 2. Schematic representation of various embodiments of the polynucleotides of the invention. The length is 200 nucleotides or less, and 11 nucleotides or greater. In c) the darker vertical bars diagrammatically represent substituted nucleotides.

Figure 3:
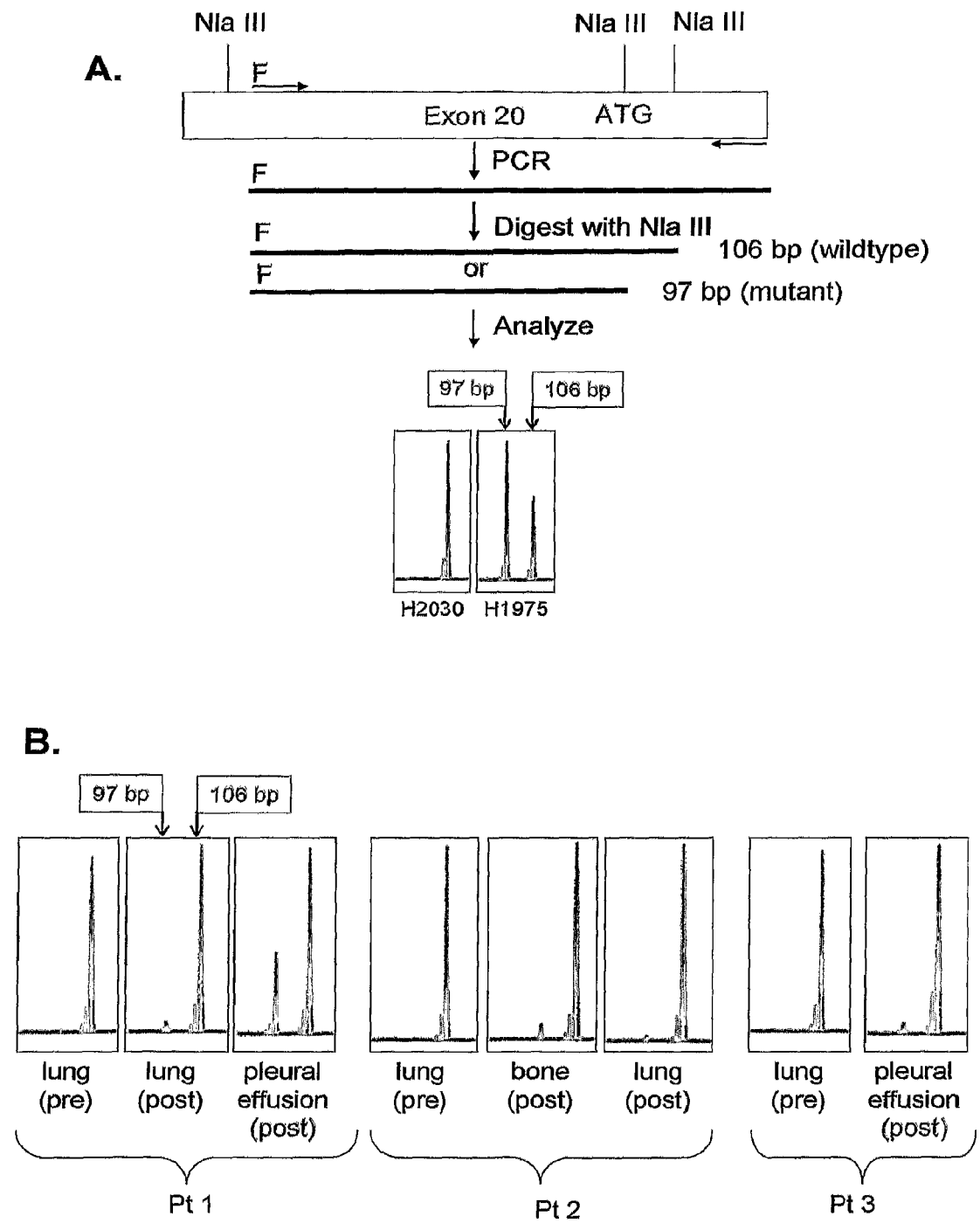
FIG. 3. A Novel PCR-RFLP Assay Independently Confimis Presence of the T790M Mutation in Exon 20 of the EGFR Kinase Domain
- (A) Design of the assay (see text for details). "F" designates a fluorescent label, such as FAM. At the bottom of this panel, the assay demonstrates with the 97-bp NlaIII cleavage product the presence of the T790M mutation in the H1975 cell line; this product is absent in H2030 DNA. The 106-bp NlaIII cleavage product is generated by digestion of wild-type EGFR.
- (B) The PCR-RFLP assay demonstrates that pre-drug tumor samples from the three patients lack detectable levels of the mutant 97-bp product, while specimens obtained after disease progression contain the T790M mutation. Pt: patient.

(B) Patient 2. CT-guided biopsy of a progressing thoracic spine lesion (left panel) and fluoroscopic-guided biopsy of a progressing lung lesion (right panel).

FIG. 6. Sequencing Chromatograms with the EGFR Exon 19 and 21 Mutations Identified in Patients 1 and 2
  (A) Status of EGFR exon 21 in tumor specimens from patient 1. DNA from the growing lung lesion and the pleural effusion demonstrated a heterozygous T→G mutation at position 2573, leading to the common L858R amino acid substitution.
  (B) All three specimens from patient 2 showed the same heterozygous exon 19 deletion, removing residues 747-749 and changing the alanine at position 750 to proline. The partial forward sequence shown for original lung tumor and growing lung lesion is Seq ID No. 16. The partial forward sequence shown for growing bine lesion is Seq ID No. 18. The partial reverse sequences shown are all Seq ID No. 17. The original four-color sequencing traces have been transformed to black-and-white.

Figure 7:
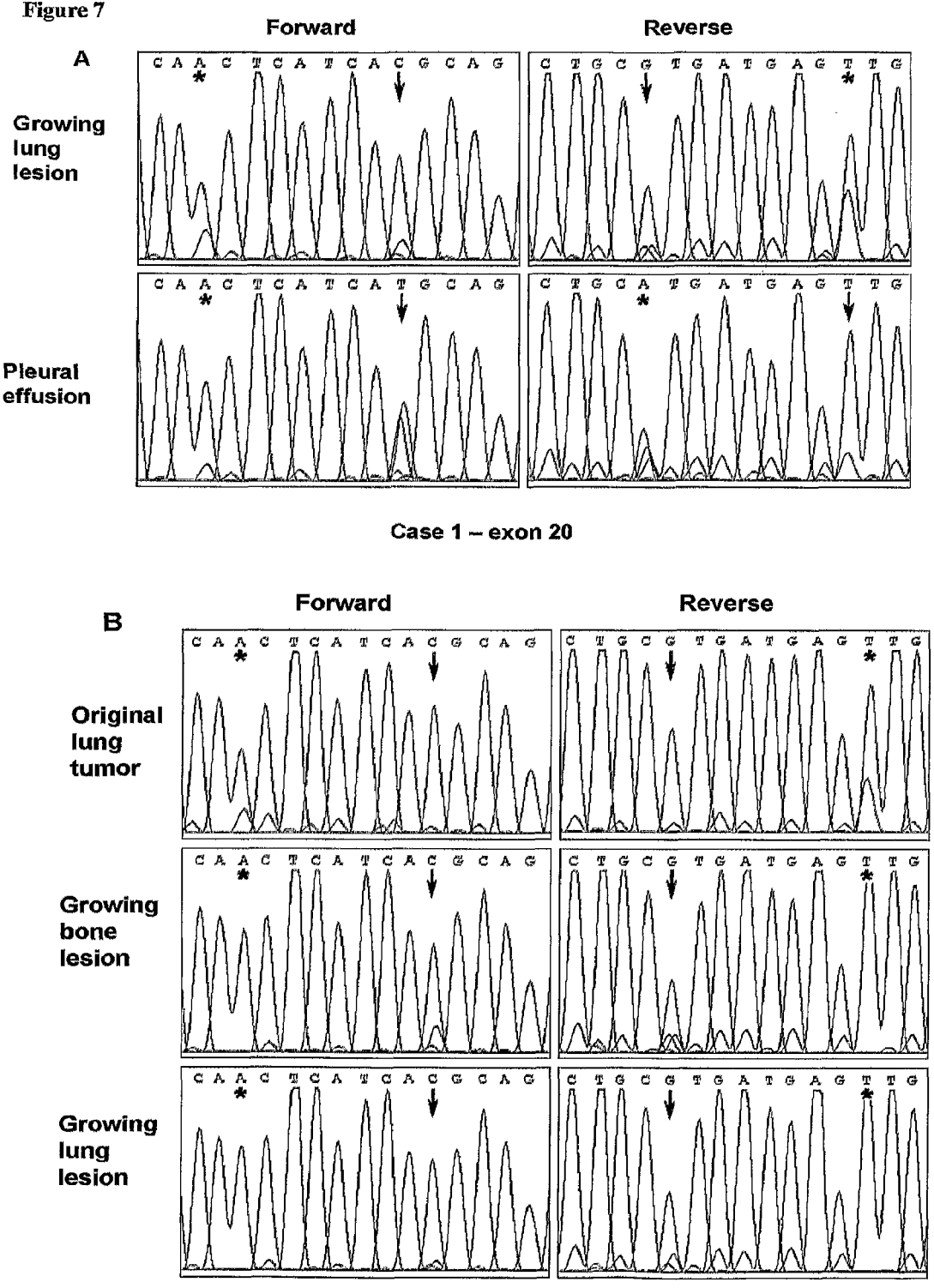
Figure 7:
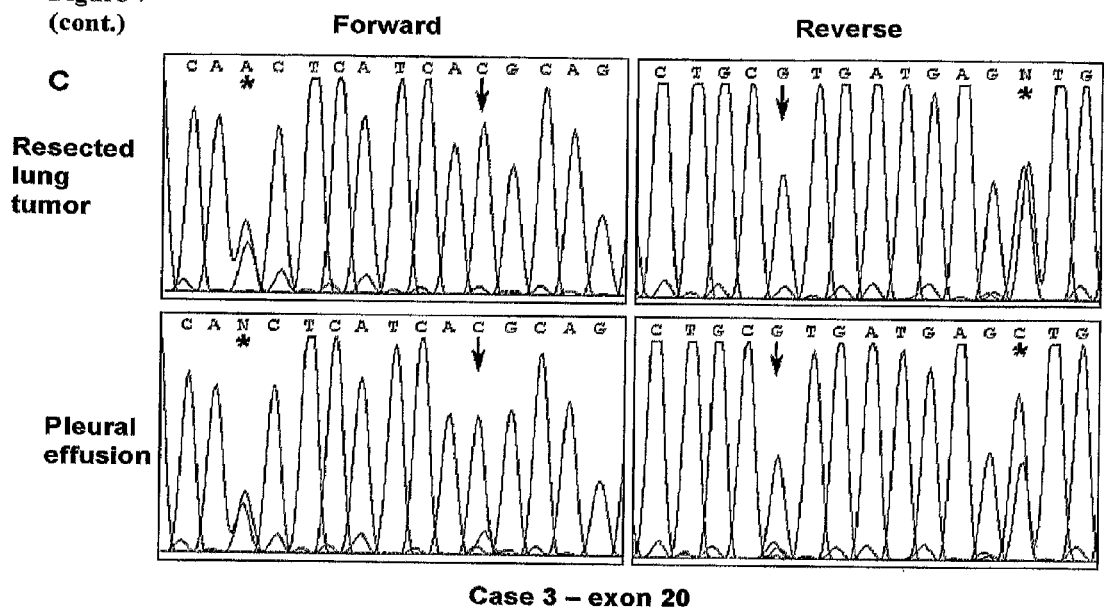
Figure 7:
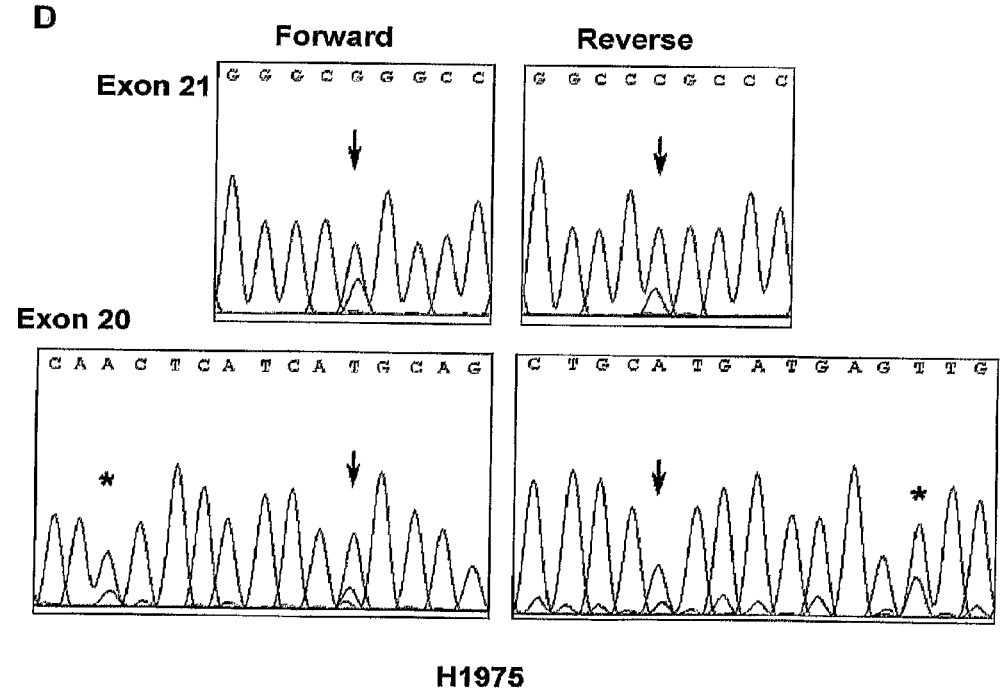

FIG. 7. Sequencing Chromatograms with the T790M EGFR Exon 20 Mutation in Various Clinical Specimens and the NSCLC Cell Line H1975. The original four-color sequencing traces have been transformed to black-and-white.
  (A-C) In all three patients—patient 1 (A), patient 2 (B), and patient 3 (C)—the secondary T790M mutation was observed only in lesions obtained after progression on either gefitinib or erlotinib. The partial forward sequence shown in FIG. 7A, for growing lung lesion, and 7B are Seq ID No. 19. The partial reserve sequence shown in FIG. 7A for growing lung lesion, and 7B are Seq ID No. 20. The partial forward sequence shown in FIG. 7A for pleural effusion is Seq ID No. 21. The partial reverse sequence shown in FIG. 7A for pleural effusion is Seq ID No. 22. The partial forward sequence shown in FIG. 7C for resected lung tumor is Seq ID No. 19. The partial reverse sequence shown in FIG. 7C for resected lung tumor is Seq ID No. 23. The partial forward sequence shown in FIG. 7C for pleural effusion is Seq ID No. 24. The partial reverse sequence shown in FIG. 7C for pleural effusion is Seq ID No. 25.
  (D) Cell line H1975 contains both an exon 21 L858R mutation (upper panel) and the exon 20 T790M mutation (lower panel). The asterisks indicate a common SNP (A or G) at nucleotide 2361; the arrows indicate the mutation at nucleotide 2369 (C→T), which leads to substitution of methionine (ATG) for threonine (ACG) at position 790. In the forward direction, the mutant T peak is blue. In the reverse direction, the mutant peak is green, while the underlying blue peak represents an "echo" from the adjacent nucleotide. The partial forward sequence shown in FIG. 7D for exon is Seq ID No. 26. The partial reverse sequence shown in FIG. 7D for exon 20 is Seq ID No. 27.

Figure 8:
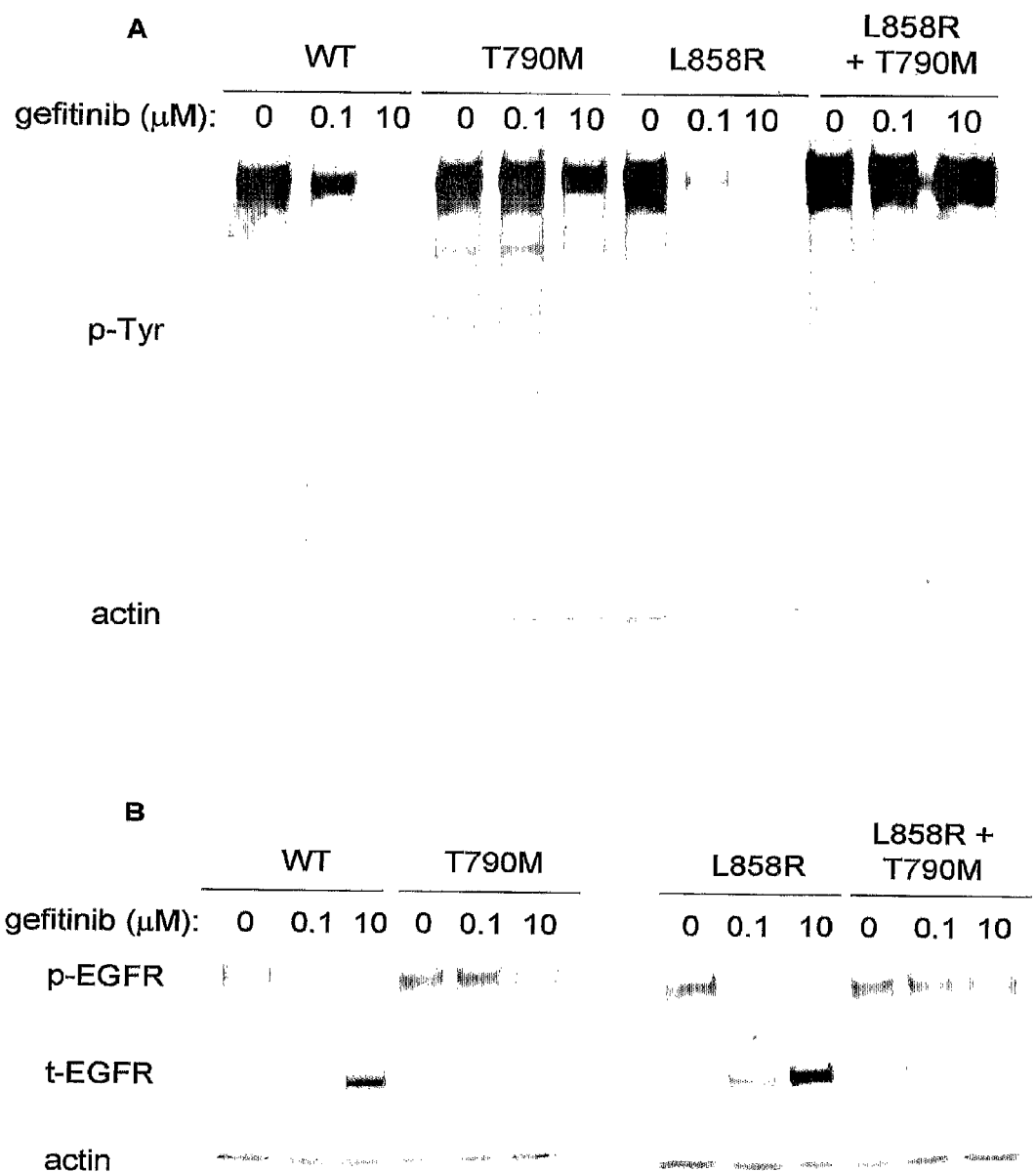
Figure 8:
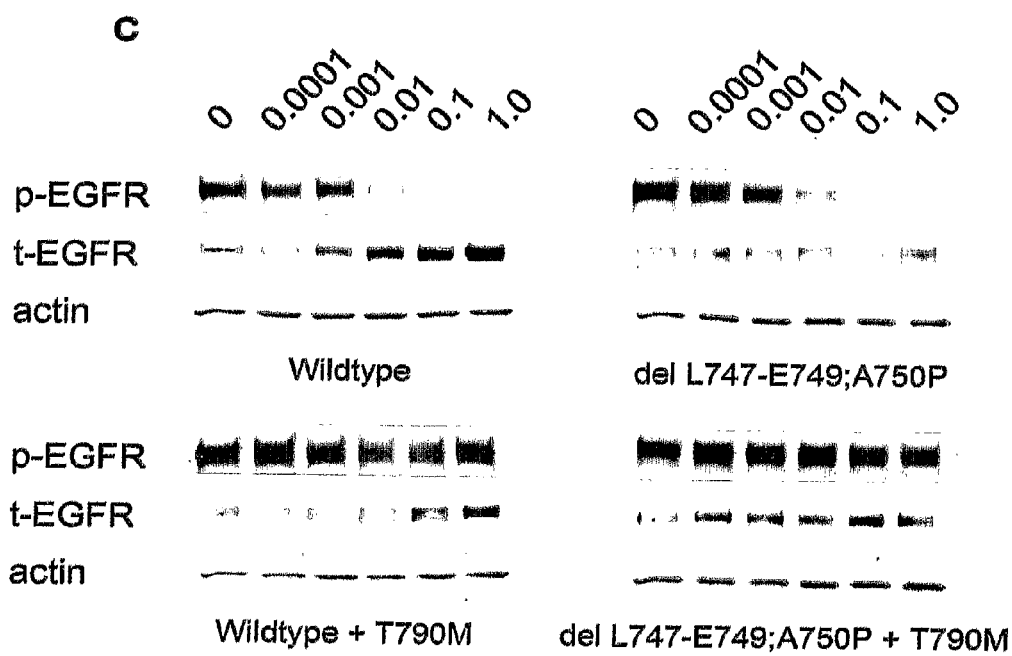

FIG. 8. EGFR Mutants Containing the T790M Mutation Are Resistant to Inhibition by Gefitinib or Erlotinib 293T cells were transiently transfected with plasmids encoding wild-type (WT) EGFR or EGFR mutants with the following changes: T790M, L858R, L858R+T790M, del L747–E749;A750P, or del L747+E749;A750P+T790M. After 36 h, cells were serum-starved for 24 h, treated with gefitinib or erlotinib for 1 h, and then harvested for immunoblot analysis using anti-p-EGFR (Y1092), anti-t-EGFR, anti-phosphotyrosine (p-Tyr), and anti-actin antibodies. The EGFR T790M mutation, in conjunction with either wild-type EGFR or the drug-sensitive L858R EGFR mutant, prevents inhibition of tyrosine phosphorylation (A) or p-EGFR (B) by gefitinib. Analogously, the T790M mutation, in conjunction with the drug-responsive del L747–E749;A750P EGFR mutant, prevents inhibition of p-EGFR by erlotinib (C).

Figure 9:
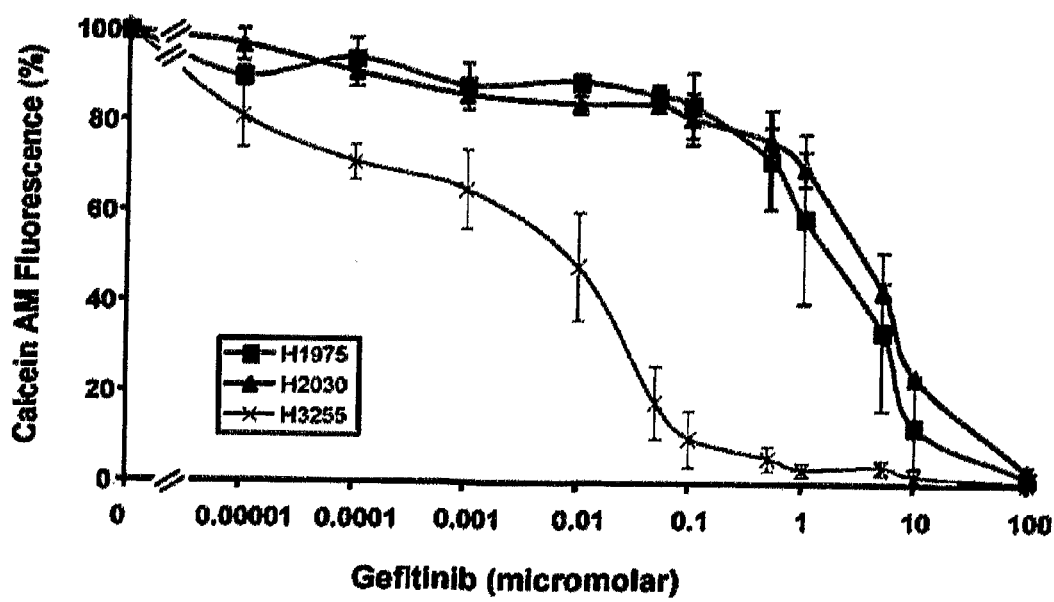

FIG. 9. Sensitivity to Gefitinib Differs Among NSCLC Cell Lines Containing Various Mutations in EGFR or KRAS The three indicated NSCLC cell lines (H3255: L858R mutation; H1975: both T790M and L858R mutations; and H2030: wild-type EGFR, mutant KRAS (see Table 7)) were grown in increasing concentrations of gefitinib, and the density of live cells after 48 hours of treatment was measured using a Calcein AM fluorescence assay. Fluorescence in vehicle-treated cells is expressed as 100%. Results are the mean±SE of three independent experiments in which there were four to eight replicates of each condition. Similar results were obtained with erlotinib.

Figure 10:
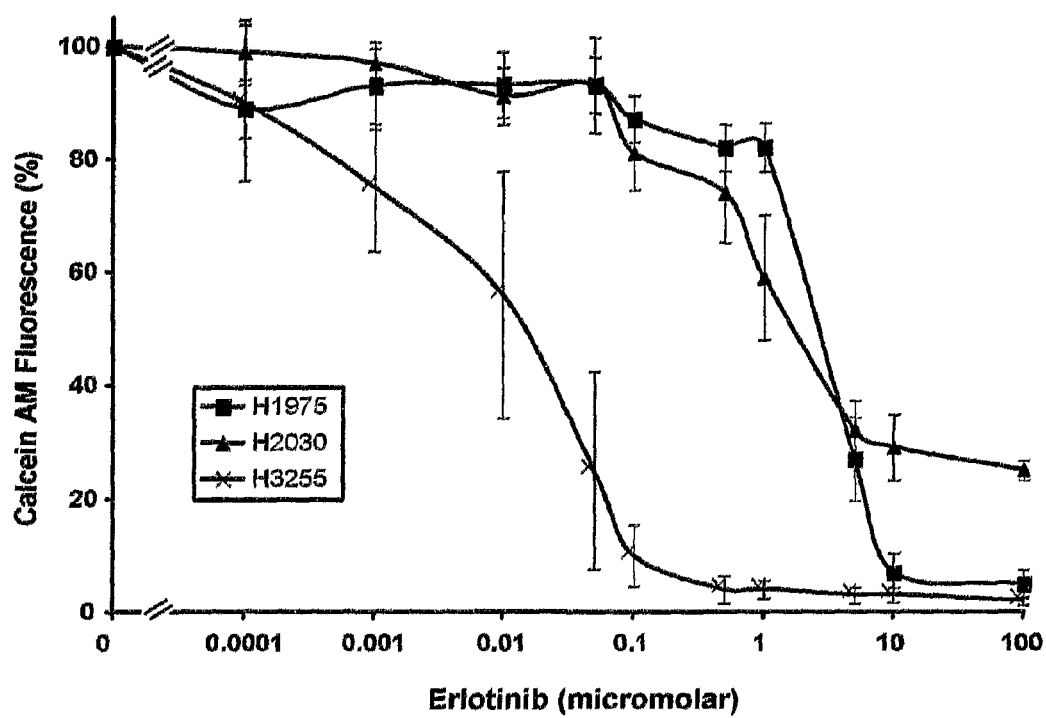

FIG. 10. Sensitivity to Erlotinib Differs among NSCLC Cell Lines Containing Various Mutations in EGFR or KRAS. See legend for FIG. 9.

DETAILED DESCRIPTION OF THE INVENTION

All patents, patent application publications, and patent applications identified herein are incorporated by reference in their entireties, as if appearing herein verbatim. All technical publications identified herein are also incorporated by reference.

Abbreviations: CML, chronic myelogenous leukemia; CT, computed tomography; del, deletion; EGFR, epidermal growth factor receptor; GIST, gastrointestinal stromal tumor; HES, hypereosinophilic syndrome; NSCLC, non-small cell lung cancer; p-EGFR, phospho-EGFR; PCR-RFLP, PCR restriction fragment length polymorphism; SNP, single nucleotide polymorphism; t-EGFR, total EGFR Accession Numbers: Reference EGFR sequence was obtained from LocusLink accession number 1956 and GenBank accession number NT 033968.

Two numbering systems are used for EGFR. The first denotes the initiating methionine in the signal sequence as amino acid −24. The second, used here, denotes the methionine as amino acid +1. Commercial suppliers of antibodies, such as the Y1068-specific anti-phospho-EGFR, use the first nomenclature. To be consistent, we consider Y1068 as Y1092. Likewise, the T790M mutation reported here has also been called T766M.

In the present description, the articles "a", "an", and "the" relate equivalently to a meaning as singular or as plural. The particular sense for these articles is apparent from the context in which they are used.

As used herein the term "tumor" refers to all neoplastic cell growth and proliferation, whether malignant or benign, and all precancerous and cancerous cells and tissues.

As used herein the term "cancer" refers to cells or tissues possessing characteristics such as uncontrolled proliferation, loss of specialized functions, immortality, significant metastatic potential, significant increase in anti-apoptotic activity, rapid growth and proliferation rate, and certain characteristic morphological and cellular markers. In some circumstances, cancer cells will be in the form of a tumor; such cells may exist locally within an animal, and in other circumstances they may circulate in the blood stream as independent cells, for example, leukemic cells.

To determine whether cancers that acquire clinical resistance to either gefitinib or erlotinib display additional mutations in the EGFR kinase domain, we have examined the status of EGFR exons 18 to 24 in tumors from thirteen patients who initially responded but subsequently progressed while on these drugs. These exons were also assessed in tumor cells from a fourteenth patient whose disease rapidly recurred while on gefitinib therapy after complete gross tumor resection. Because of the association of KRAS mutations with primary resistance to gefitinib and erlotinib [7], we also examined the status of KRAS in tumor cells from these six patients. In an effort to explain the selective advantage of cells with a newly identified "resistance" mutation in EGFR—a T790M amino acid substitution (also known as T766M), a 2369 C→T change in the EGFR genomic sequence—we further characterized the drug sensitivity of putatively resistant EGFR mutants versus wild-type or drug-sensitive EGFR mutants, using both a NSCLC cell line fortuitously found to contain the T790M mutation and lysates from cells transiently transfected with wild-type and mutant EGFR cDNAs.

SEQ ID NO:1 (shown in Table 1) displays the cDNA sequence of the mutant human EGFR gene. The pair of primers used to amplify the EGFR fragment used for sequencing to detect the presence or absence of the EGFR T790M mutation is underlined and in italic font. The mutant t2369 nucleotide is shown in enlarged bold font. The wild type EGFR sequence is known from GenBank Accession No. X00588, and Ullrich, A. et al. "Human epidermal growth factor receptor cDNA sequence and aberrant expression of the amplified gene in A431 epidermoid carcinoma cells", Nature 309 (5967), 418-425 (1984). The translated mutant protein sequence is shown in SEQ ID NO:2 (Table 2). The mutant M790 is shown in enlarged bold font.

TABLE 1

2369 C→T MUTANT EGFR cDNA (SEQ ID NO: 1)
atgcgaccctccgggacggccggggcagcgctcctggcgctgctggctgcgtctgcccggcgagtcg ggctctggaggaaaagaaagtttgccaaggcacgagtaacaagctcacgcagttgggcacttttgaag atcattttctcagcctccagaggatgttcaataactgtgaggtggtccttgggaatttggaaattacc tatgtgcagaggaattatgatcttttccttcttaaagaccatccaggaggtggctggttatgtcctcat tgccctcaacacagtggagcgaattcctttggaaaacctgcagatcatcagaggaaatatgtactacg aaaattcctatgccttagcagtcttatctaactatgatgcaaataaaaccggactgaaggagctgccc atgagaaatttacaggaaatcctgcatggcgccgtgcggttcagcaacaaccctgccctgtgcaacgt ggagagcatccagtggcgggacatagtcagcagtgactttctcagcaacatgtcgatggacttccaga accacctgggcagctgccaaaagtgtgatccaagctgtcccaatgggagctgctggggtgcaggagag gagaactgccagaaactgaccaaaatcatctgtgcccagcagtgctccgggcgctgccgtggcaagtc ccccagtgactgctgccacaaccagtgtgctgcaggctgcacaggcccccgggagagcgactgcctgg tctgccgcaaattccgagacgaagccacgtgcaaggacacctgcccccccactcatgctctacaacccc accacgtaccagatggatgtgaaccccgagggcaaatacagctttggtgccacctgcgtgaagaagtg tccccgtaattatgtggtgacagatcacggctcgtgcgtccgagcctgtggggccgacagctatgaga tggaggaagacggcgtccgcaagtgtaagaagtgcgaagggccttgccgcaaagtgtgtaacggaata ggtattggtgaatttaaagactcactctccataaatgctacgaatattaaacacttcaaaaactgcac ctccatcagtggcgatctccacatcctgccggtggcatttaggggtgactccttcacacatactcctc ctctggatccacaggaactggatattctgaaaaccgtaaaggaaatcacagggttttgctgattcag gcttggcctgaaaacaggacggacctccatgcctttgagaacctagaaatcatacgcggcaggaccaa gcaacatggtcagttttctcttgcagtcgtcagcctgaacataacatccttgggattacgctccctca aggagataagtgatggagatgtgataatttcaggaaacaaaaatttgtgctatgcaaatacaataaac tggaaaaaactgtttgggacctccggtcagaaaaccaaaattataagcaacagaggtgaaaacagctg caaggccacaggccaggtctgccatgccttgtgctccccgagggctgctggggcccggagcccaggg actgcgtctcttgccggaatgtcagccgaggcagggaatgcgtggacaagtgcaaccttctggagggt gagccaagggagtttgtggagaactctgagtgcatacagtgccacccagagtgcctgcctcaggccat gaacatcacctgcacaggacggggaccagacaactgtatccagtgtgcccactacattgacggccccc actgcgtcaagacctgcccggcaggagtcatgggagaaaacaacaccctggtctggaagtacgcagac gccgccatgtgtgccacctgtgccatccaaactgcacctacggatgcactgggccaggtcttgaagg ctgtccaacgaatgggcctaagatcccgtccatcgccactgggatggtgggggccctcctcttgctgc

TABLE 1-continued

2369 C→T MUTANT EGFR cDNA tggtggtggccctggggatcggcctcttcatgcgaaggcgccacatcgttcggaagcgcacgctgcgg aggctgctgcaggagagggagcttgtggagcctcttacacccagtggagaagct*cccaaccaagctct*

*cttgag*gatcttgaaggaaactgaattcaaaaagatcaaagtgctgggctccggtgcgttcggcacgg tgtataagggactctggatcccagaaggtgagaaagttaaaattcccgtcgctatcaaggaattaaga gaagcaacatctccgaaagccaacaaggaaatcctcgatgaagcctacgtgatggcagcgtggacaa ccccacgtgtgccgcctgctgggcatctgcctcacctccaccgtgcagctcatcatgcagctcatgc ccttcggctgcctcctggactatgtccgggaacacaaagacaatattggctcccagtacctgctcaac tggtgtgtgcagatcgcaaagggcatgaactacttggaggaccgtcgcttggtgcaccgcgacctggc agccaggaacgtactggtgaaaacaccgcagcatgtcaagatcacagattttgggctggccaaactgc tgggtgcggaagagaaagaataccatgcagaaggaggcaaagtgcctatcaagtggatggcattggaa tcaattttacacagaatctatacccaccagagtgatgtctggagctacggggtgaccgtttgggagtt gatgacctttggatccaagccatatgacggaatccctgccagcgagatctcctccatcctggagaaag gagaacgctcccctcagccacccatatgtaccatcgatgtctacatgatcatggtcaagtgctggatg atagacgcagatagtcgcccaaagttccgtgagttgatcatcgaattctccaaaatggcccgaga*ccc*

*ccagcgctaccttgtcatt*caggggatgaaagaatgcatttgccaagtcctacagactccaacttct accgtgccctgatggatgaagaagacatggacgacgtggtggatgccgacgagtacctcatcccacag cagggcttcttcagcagcccctccacgtcacggactcccctcctgagctctctgagtgcaaccagcaa caattccaccgtggcttgcattgatagaaatgggctgcaaagctgtcccatcaaggaagacagcttct tgcagcgatacagctcagaccccacaggcgccttgactgaggacagcatagacgacaccttcctccca gtgcctgaatacataaaccagtccgttcccaaaaggcccgctggctctgtgcagaatcctgtctatca caatcagcctctgaaccccgcgcccagcagagacccacactaccaggaccccacagcactgcagtgg gcaaccccgagtatctcaacactgtccagcccacctgtgtcaacagcacattcgacagccctgcccac tgggcccagaaaggcagccaccaaattagcctggacaaccctgactaccagcaggacttctttcccaa ggaagccaagccaaatggcatctttaagggctccacagctgaaaatgcagaatacctaagggtcgcgc cacaaagcagtgaatttattggagcatga

TABLE 2

T790M MUTANT EGFR (SEQ ID NO: 2)
MRPSGTAGAALLALLAALCPASRALEEKKVCQGTSNKLTQLGTFEDHFLSLQRMFNNCEVVLGNLEIT

YVQRNYDLSFLKTIQEVAGYVLIALNTVERIPLENLQIIRGNMYYENSYALAVLSNYDANKTGLKELP

MRNLQEILHGAVRFSNNPALCNVESIQWRDIVSSDFLSNMSMDFQNHLGSCQKCDPSCPNGSCWGAGE

ENCQKLTKIICAQQCSGRCRGKSPSDCCHNQCAAGCTGPRESDCLVCRKFRDEATCKDTCPPLMLYNP

TTYQMDVNPEGKYSFGATCVKKCPRNYVVTDHGSCVRACGADSYEMEEDGVRKCKKCEGPCRKVCNGI

GIGEFKDSLSINATNIKHFKNCTSISGDLHILPVAFRGDSFTHTPPLDPQELDILKTVKEITGFLLIQ

AWPENRTDLHAFENLEIIRGRTKQHGQFSLAVVSLNITSLGLRSLKEISDGDVIISGNKNLCYANTIN

WKKLFGTSGQKTKIISNRGENSCKATGQVCHALCSPEGCWGPEPRDCVSCRNVSRGRECVDKCKLLEG

EPREFVENSECIQCHPECLPQAMNITCTGRGPDNCIQCAHYIDGPHCVKTCPAGVMGENNTLVWKYAD

AGHVCHLCHPNCTYGCTGPGLEGCPTNGPKIPSIATGMVGALLLLLVVALGIGLFMRRRHIVRKRTLR

TABLE 2-continued

T790M MUTANT EGFR

RLLQERELVEPLTPSGEAPNQALLRILKETEFKKIKVLGSGAFGTVYKGLWIPEGEKVKIPVAIKELR

EATSPKANKEILDEAYVMASVDNPHVCRLLGICLTSTVQLIMQLMPFGCLLDYVREHKDNIGSQYLLN

WCVQIAKGMNYLEDRRLVHRDLAARNVLVKTPQHVKITDFGLAKLLGAEEKEYHAEGGKVPIKWMALE

SILHRIYTHQSDVWSYGVTVWELMTFGSKPYDGIPASEISSILEKGERLPQPPICTIDVYMIMVKCWM

IDADSRPKFRELIIEFSKMARDPQRYLVIQGDERMHLPSPTDSNFYRALMDEEDMDDVVDADEYLIPQ

QGFFSSPSTSRTPLLSSLSATSNNSTVACIDRNGLQSCPIKEDSFLQRYSSDPTGALTEDSIDDTFLP

VPEYINQSVPKRPAGSVQNPVYHNQPLNPAPSRDPHYQDPHSTAVGNPEYLNTVQPTCVNSTFDSPAH

WAQKGSHQISLDNPDYQQDFFPKEAKPNGIFKGSTAENAEYLRVAPQS

As used herein, a "nucleic acid" or "polynucleotide", and similar terms and phrases, relate to polymers composed of naturally occurring nucleotides as well as to polymers composed of synthetic or modified nucleotides. Thus, as used herein, a polynucleotide that is a RNA, or a polynucleotide that is a DNA, or a polynucleotide that contains both deoxyribonucleotides and ribonucleotides, may include naturally occurring moieties such as the naturally occurring bases and ribose or deoxyribose rings, or they may be composed of synthetic or modified moieties such as those described below. A polynucleotide employed in the invention may be single stranded or it may be a base paired double stranded structure, or even a triple stranded base paired structure.

Nucleic acids and polynucleotides may be 20 or more nucleotides in length, or 30 or more nucleotides in length, or 50 or more nucleotides in length, or 100 or more, or 1000 or more, or tens of thousands or more, or hundreds of thousands or more, in length. As used herein, "oligonucleotides" and similar terms based on this relate to short polymers composed of naturally occurring nucleotides as well as to polymers composed of synthetic or modified nucleotides, as described in the immediately preceding paragraph. Oligonucleotides may be 10 or more nucleotides in length, or 20 or more nucleotides in length, or 30 or more nucleotides in length, or 40 or more, up to about 50, nucleotides in length. Oligonucleotides may be chemically synthesized and may be used as PCR primers, or probes, among other uses.

It is understood that, because of the overlap in size ranges provided in the preceding paragraph, the terms "polynucleotide" and "oligonucleotide" may be used synonymously herein to refer to primer or a probe of the invention.

As used herein "nucleotide sequence", "oligonucleotide sequence" or "polynucleotide sequence", and similar terms, relate interchangeably both to the sequence of bases that an oligonucleotide or polynucleotide has, as well as to the oligonucleotide or polynucleotide structure possessing the sequence. A nucleotide sequence or a polynucleotide sequence furthermore relates to any natural or synthetic polynucleotide or oligonucleotide in which the sequence of bases is defined by description or recitation of a particular sequence of letters designating bases as conventionally employed in the field.

A "nucleoside" is conventionally understood by workers of skill in fields such as biochemistry, molecular biology, genomics, and similar fields related to the field of the invention as comprising a monosaccharide linked in glycosidic linkage to a purine or pyrimidine base; and a "nucleotide" comprises a nucleoside with at least one phosphate group appended, typically at a 3' or a 5' position (for pentoses) of the saccharide, but may be at other positions of the saccharide. Nucleotide residues occupy sequential positions in an oligonucleotide or a polynucleotide. A modification or derivative of a nucleotide may occur at any sequential position in an oligonucleotide or a polynucleotide. All modified or derivatized oligonucleotides and polynucleotides are encompassed within the invention and fall within the scope of the claims. Modifications or derivatives can occur in the phosphate group, the monosaccharide or the base.

By way of nonlimiting examples, the following descriptions provide certain modified or derivatized nucleotides, all of which are within the scope of the polynucleotides of the invention. The monosaccharide may be modified by being, for example, a pentose or a hexose other than a ribose or a deoxyribose. The monosaccharide may also be modified by substituting hydryoxyl groups with hydro or amino groups, by alkylating or esterifying additional hydroxyl groups, and so on. Substituents at the 2' position, such as 2'-O-methyl, 2'-O-ethyl, 2'-O-propyl, 2'-O-allyl, 2'-O-aminoalkyl or 2'-deoxy-2'-fluoro group provide enhanced hybridization properties to an oligonucleotide.

The bases in oligonucleotides and polynucleotides may be "unmodified" or "natural" bases include the purine bases adenine (A) and guanine (G), and the pyrimidine bases thymine (T), cytosine (C) and uracil (U). In addition they may be bases with modifications or substitutions. Nonlimiting examples of modified bases include other synthetic and natural bases such as hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine, 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil, 5-halo-cytosine, 5-propy-uracil, 5-propynyl-cytosine and other alkynyl derivatives of pyrimidine bases, 6-azo-uracil, 6-azo-cytosine, 6-azo-thymine, 5-uracil (pseudouracil), 4-thiouracil, 8-halo, 8-amino-, 8-thiol-, 8-thioalkyl-, 8-hydroxyl- and other 8-substituted adenines and guanines, 5-halo particularly 5-bromo, 5-trifluoromethyl and other 5-substituted uracils and cytosines, 7-methylguanine and 7-methyladenine, 2-fluoro-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine (1H-pyrimido[5,4-b][1,4]benzoxazin-2(3H)-one), phenothiazine cytidine (1-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified bases may also include those in which the purine or pyrimidine base is replaced with other heterocycles, for example 7-deaza-adenine, 7-deazaguanosine, 2-aminopyridine and 2-pyridone. Further bases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition (1991) 30, 613, and those disclosed by Sanghvi, Y. S., Chapter 15, Antisense Research and Applications, pages 289-302, Crooke, S. T. and Lebleu, B., ed., CRC Press, 1993. Certain of these bases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2.degree. C. (Sanghvi, Y. S., Crooke, S. T. and Lebleu, B., eds., Antisense Research and Applications, CRC Press, Boca Raton, 1993, pp. 276-278) and are presently preferred base substitutions, even more particularly when combined with 2'-O-methoxyethyl sugar modifications. See U.S. Pat. Nos. 6,503,754 and 6,506,735 and references cited therein, incorporated herein by reference. Modifications further include those disclosed in U.S. Pat. Nos. 5,138,045 and 5,218,105, drawn to polyamine conjugated oligonucleotides; U.S. Pat. Nos. 5,212,295, 5,521,302, 5,587,361 and 5,599,797, drawn to oligonucleotides incorporating chiral phosphorus linkages including phosphorothioates; U.S. Pat. Nos. 5,378,825, 5,541,307, and 5,386,023,drawn to oligonucleotides having modified backbones; U.S. Pat. Nos. 5,457,191 and 5,459,255, drawn to modified nucleobases; U.S. Pat. No. 5,539,082, drawn to peptide nucleic acids; U.S. Pat. No. 5,554,746, drawn to oligonucleotides having beta-lactam backbones; U.S. Pat. No. 5,571,902, disclosing the synthesis of oligonucleotides; U.S. Pat. No. 5,578,718, disclosing alkylthio nucleosides; U.S. Pat. No. 5,506,351, drawn to 2'-O-alkyl guanosine, 2,6-diaminopurine, and related compounds; U.S. Pat. No. 5,587,469, drawn to oligonucleotides having N-2 substituted purines; U.S. Pat. No. 5,587,470, drawn to oligonucleotides having 3-deazapurines; U.S. Pat. No. 5,223,168, and U.S. Pat. No. 5,608,046, drawn to conjugated 4'-desmethyl nucleoside analogs; U.S. Pat. Nos. 5,602,240, and 5,610,289, drawn to backbone-modified oligonucleotide analogs; U.S. Pat. Nos. 6,262,241, and 5,459,255, drawn to, inter alia, methods of synthesizing 2'-fluoro-oligonucleotides.

The linkages between nucleotides is commonly the 3'-5' phosphate linkage, which may be a natural phosphodiester linkage, a phosphothioester linkage, and still other synthetic linkages. Oligonucleotides containing phosphorothioate backbones have enhanced nuclease stability. Examples of modified backbones include, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates. Additional linkages include phosphotriester, siloxane, carbonate, carboxymethylester, acetamidate, carbamate, thioether, bridged phosphoramidate, bridged methylene phosphonate, bridged phosphorothioate and sulfone internucleotide linkages. Other polymeric linkages include 2'-5' linked analogs of these. See U.S. Pat. Nos. 6,503,754 and 6,506,735 and references cited therein, incorporated herein by reference.

Any modifications including those exemplified in the above description can readily be incorporated into, and are comprised within the scope of, the polynucleotides of the invention. Use of any modified nucleotide is equivalent to use of a naturally occurring nucleotide having the same base-pairing properties, as understood by a worker of skill in the art. All equivalent modified nucleotides fall within the scope of the present invention as disclosed and claimed herein.

As used herein and in the claims, the term "complement", "complementary", "complementarity", and similar words and phrases, relate to two sequences whose bases form complementary base pairs, base by base, as conventionally understood by workers of skill in fields such as biochemistry, molecular biology, genomics, and similar fields related to the field of the invention. Two single stranded (ss) polynucleotides having complementary sequences can hybridize with each other under suitable buffer and temperature conditions to form a double stranded (ds) polynucleotide. By way of nonlimiting example, if the naturally occurring bases are considered, A and (T or U) interact with each other, and G and C interact with each other. Unless otherwise indicated, "complementary" is intended to signify "fully complementary", namely, that when two polynucleotide strands are aligned with each other, there will be at least a portion of the strands in which each base in a sequence of contiguous bases in one strand is complementary to an interacting base in a sequence of contiguous bases of the same length on the opposing strand.

As used herein, "liberate" and similar words and phrases, when used in connection with a nucleic acid, relate to a process whereby a cell or a tissue is treated sufficiently to make the nucleic acids contained therein available for interaction with reagents, including PCR primers, employed in methods of the present invention.

As used herein, "hybridize", "hybridization" and similar words and phrases relate to a process of forming a nucleic acid, polynucleotide, or oligonucleotide duplex by causing strands with complementary sequences to interact with each other. The interaction occurs by virtue of complementary bases on each of the strands specifically interacting to form a pair. The ability of strands to hybridize to each other depends on a variety of conditions, as set forth below. Nucleic acid strands hybridize with each other when a sufficient number of corresponding positions in each strand are occupied by nucleotides that can interact with each other. Polynucleotide strands that hybridize to each other may be fully complementary. Alternatively, two hybridized polynucleotides may be "substantially complementary" to each other, indicating that they have a small number of mismatched bases. Both naturally occurring bases, and modified bases such as those described herein, participate in forming complementary base pairs. It is understood by workers of skill in the field of the present invention, including by way of nonlimiting example biochemists and molecular biologists, that the sequences of strands forming a duplex need not be 100% complementary to each other to be specifically hybridizable.

As used herein "fragment" and similar words and phrases relate to portions of a nucleic acid, polynucleotide or oligonucleotide shorter than the full sequence of a reference. The sequence of bases in a fragment is unaltered from the sequence of the corresponding portion of the reference; there are no insertions or deletions in a fragment in comparison with the corresponding portion of the reference.

As used herein "cleaving means" and similar terms and phrases relate to a substance that cleaves a polynucleotide in a sequence-specific fashion. The cleaving means interacts only with a polynucleotide at a susceptible subsequence of bases present therein, and cleaves the polynucleotide into two smaller pieces. Nonlimiting examples of cleaving means include restriction nucleases, sequence-specific ribozymes, aptamers with cleaving activity, and sequence-specific organic molecules with cleaving activity. Any equivalent cleaving means known to workers of skill in the field of the invention are within the scope of the invention.

"Complementary DNA" (cDNA), is a single-stranded DNA molecule that is copied from an mRNA template by the enzyme reverse transcriptase, resulting in a sequence complementary to that of the mRNA. Those skilled in the art also use the term "cDNA" to refer to a double-stranded DNA molecule that comprises such a single-stranded DNA molecule and its complementary DNA strand.

Various methods are provided for detecting the presence of EGFR T790M mutation contained in a sample (cancer tissue biopsy, cancer cells obtained by laser tissue capture from a biopsy or cancer cells isolated from serum). Such methods can include contacting a DNA sample with two primers that are upstream and downstream of the EGFR T790M region, amplifying the EGFR T790M region according to standard procedures, and detecting whether the amplified sequence is present or absent in the nucleic acid sample. Accordingly, primers capable of recognizing and binding to EGFR T790M upstream and downstream region and nucleic acid probes having an affinity to EGFR T790M mutation are preferred means of supporting such methods. For example, the whole EGFR exon 20 can be amplified by PCR using genomic DNA as template and using primer pairs capable of recognizing and binding, respectively, to the 5' and 3' intron flanking sequences of exon 20 (such exon 20 flanking sequences are indicated with capital letters in SED ID NO:3 (Table 3, see GenBank Acc. No NT_033968). Such primer pairs that include nucleotide 2369 of the EGFR cDNA sequence can amplify a fragment that it can then be used for sequencing, restriction length polymorphism analysis or any other technique for determining the presence or absence of the 2369 C→T mutation.

TABLE 3

(SEQ ID NO: 3)

```
161101 TTTAGCTTCC TCAGCCCAAG AATAGCAGAA GGGTTAAAAT AAAGTCTGTA TTTATGGCTC

161161 TGTCAAAGGA AGGCCCCTGC CTTGGCAGCC AGCCGGAATT AGCAGGGCAG CAGATGCCTG

161221 ACTCAGTGCA GCATGGATTT CCCATAGGGA GCCTGGGGGC ACAGCACAGA GAGACCACTT

161281 CTCTTTAGAA ATGGGTCCCG GGCAGCCAGG CAGCCTTTAG TCACTGTAGA TTGAATGCTC

161341 TGTCCATTTC AAAACCTGGG ACTGGTCTAT TGAAAGAGCT TATCCAGCTA CTCTTTGCAG

161401 AGGTGCTGTG GGCAGGGTCC CCAGCCCAAA TGCCCACCCA TTTCCCAGAG CACAGTCAGG

161461 GCCAAGCCTG GCCTGTGGGG AAGGGAGGCC TTTCTCCCTG CTGGCTCGGT GCTCCCCGGA

161521 TGCCTTCTCC ATCGCTTGTC CTCTGCAGCA CCCACAGCCA GCGTTCCTGA TGTGCAGGGT

161581 CAGTCATTAC CCAGGGTGTT CCGGACCCCA CACAGATTCC TACAGGCCCT CATGATATTT

161641 TAAAACACAG CATCCTCAAC CTTGAGGCGG AGGTCTTCAT AACAAAGATA CTATCAGTTC

161701 CCAAACTCAG AGATCAGGTG ACTCCGACTC CTCCTTTATC CAATGTGCTC CTCATGGCCA

161761 CTGTTGCCTG GGCCTCTCTG TCATGGGGAA TCCCCAGATG CACCCAGGAG GGGCCCTCTC

161821 CCACTGCATC TGTCACTTCA CAGCCCTGCG TAAACGTCCC TGTGCTAGGT CTTTTGCAGG

161881 CACAGCTTTT CCTCCATGAG TACGTATTTT GAAACTCAAG ATCGCATTCA TGCGTCTTCA

161941 CCTGGAAGGG GTCCATGTGC CCCTCCTTCT GGCCACCATG CGAAGCCACA CTGACGTGCC

162001 TCTCCCTCCC TCCAGgaagc ctacgtgatg gccagcgtgg acaaccccca cgtgtgccgc 162061 ctgctgggca tctgcctcac ctccaccgtg cagctcatca cgcagctcat gcccttcggc 162121 tgcctcctgg actatgtccg ggaacacaaa gacaatattg gctcccagta cctgctcaac 162181 tggtgtgtgc agatcgcaaa gGTAATCAGG GAAGGGAGAT ACGGGGAGGG GAGATAAGGA

162241 GCCAGGATCC TCACATGCGG TCTGCGCTCC TGGGATAGCA AGAGTTTGCC ATGGGGATAT

162301 GTGTGTGCGT GCATGCAGCA CACACACATT CCTTTATTTT GGATTCAATC AAGTTGATCT

162361 TCTTGTGCAC AAATCAGTGC CTGTCCCATC TGCATGTGGA AACTCTCATC AATCAGCTAC
```

TABLE 3-continued

```
162421 CTTTGAAGAA TTTTCTCTTT ATTGAGTGCT CAGTGTGGTC TGATGTCTCT GTTCTTATTT

162481 CTCTGGAATT CTTTGTGAAT ACTGTGGTGA TTTGTAGTGG AGAAGGAATA TTGCTTCCCC

162541 CATTCAGGAC TTGATAACAA GGTAAGCAAG CCAGGCCAAG GCCAGGAGGA CCCAGGTGAT

162601 AGTGGTGGAG TGGAGCAGGT GCCTTGCAGG AGGCCCAGTG AGGAGGTGCA AGGAGCTGAC

162661 AGAGGGCGCA GCTGCTGCTG CTATGTGGCT GGGGCCTTGG CTAAGTGTCC CCCTTTCCAC

162721 AGGCTCGCTC CAGAGCCAGG GCGGGGCTGA GAGAGCAGAG TGGTCAGGTA GCCCTGCCTG

162781 GGTGCTGGAG ACAGGCACAG AACAACAAGC CAGGTATTTC ACAGCTGGTG CGGACCCAGA

162841 AAGACTTCTG CTTTTGCCCC AAACCCCTCC CATCTCCATC CCAGTCTTGC ATCAGTTATT

162901 TGCACTCAAC TTGCTAAGTC CTATTTTTTT CTAACAATGG GTATACATTT CATCCCATTG

162961 ACTTTAAAGG ATTTGCAGGC AGGCCCTGTC TCTGAGAATA CGCCGTTGCC CGTCATCTCT

163021 CTCCGACAGC AGGGCAGGGG GTCCAGAGAT GTGCCAGGGA CCAGAGGGAG GGAGCAGACA

163081 CCCACCCGGC CTGGGCAGGT CCTCCTCATT GCTTGCATCC GCCTGGTTAG CAGTGGCAGT

163141 CAGTCCTGCC GAGTCATTCG TGAGGCGCTC ACCCAACTCC AGGCAGATGT AAAAGGTGAC

163201 CTACAAGAAG ACAAACAAAA ACATCTGGAG CGCTCTTATG CCAGCATCTG CCCTTGACAC
```

Without limiting to these diagnostic methods, a method is provided for detecting EGFR T790M mutation whereby a restriction enzyme is used to recognize the lack or presence of a restriction site at the allelic codon. A restriction site leading to productive cleaving of the polynucleotide occurs, using a suitably selective restriction nuclease, when one or the other of the wild type or the polymorphic allele is present.

Also envisioned in the present invention is a diagnostic kit for detecting mutant EGFR T790M related malignancy in a human. Such a kit preferably includes multiple containers wherein included is a set of primers useful for PCR detection of the EGFR T790M mutation, and optionally a positive control comprising mutated EGFR sequence and a negative control comprising a non-mutated EGFR sequence.

FIG. 2 provides schematic representations of certain embodiments of the primers of the invention. The invention discloses sequences that serve as primers to amplify segments of genomic or cDNA sequences of EGFR that include the base corresponding to position 2369 of EGFR cDNA. The disclosed primer sequences, such as SEQ ID NOS:4-7 and 12-15, are represented schematically by the lightly shaded blocks in FIG. 2. FIG. 2, a) illustrates an embodiment in which the disclosed primer shown as "SEQ" may optionally be included in a larger polynucleotide whose overall length may range up to 200 nucleotides.

The invention further provides a primer sequence that is a fragment of any of the above primer sequences, SEQ ID NOS:4-7 and 12-15, that is at least 11 nucleotides in length (and at most 1 base shorter than the reference SEQ ID NO: illustrated in FIG. 2, b)), as well as a primer sequence wherein up to 5 nucleotides may differ from the sequences given in SEQ ID NOS:4-7 and 12-15 (illustrated in FIG. 2, c), showing, in this example, three variant bases represented by the three darker vertical bars).

Still further the invention provides a sequence that is a complement to any of the above-described sequences (shown in FIG. 2, d), and designated as "COMPL"). Any of these sequences are included in the oligonucleotides or polynucleotides of the invention. As noted, any primer polynucleotide of the invention optionally may include additional bases up to the limit of 200 nucleotides.

Primers of the invention are designed to be "substantially" complementary to each strand of the genomic locus or cDNA to be amplified. This means that the primers must be sufficiently complementary to hybridize with their respective strands under conditions which allow the polymerase chain reaction to proceed. In other words, the primers should have sufficient complementarity with the 5' and 3' sequences flanking the mutation to hybridize therewith and permit amplification of the genomic locus. Thus it is envisioned herein that a primer sequence need not be fully complementary to its target sequence. "Substantially identical" and similar phrases that refer to oligonucleotide sequences thus describes the functional ability to hybridize or anneal with sufficient specificity to distinguish between the presence or absence of a mutation, such as a SNP identified herein. This is measurable by the temperature of melting being sufficiently different to permit easy identification of whether the oligonucleotide is binding to the normal or mutant EGFR T790M gene sequence. Oligonucleotide primers of the invention are employed in the amplification process which is an enzymatic chain reaction that produces exponential quantities of polymorphic locus relative to the number of reaction steps involved. Typically, one primer is complementary to the negative (−) strand of the polymorphic locus and the other is complementary to the positive (+) strand. Annealing the primers to denatured nucleic acid followed by extension with an enzyme, DNA polymerase, and nucleotides, results in newly synthesized + and − strands containing the target polymorphic locus sequence. Because these newly synthesized sequences are also templates, repeated cycles of denaturing, primer annealing, and extension results in exponential production of the region (i.e., the target polymorphic locus sequence) defined by the primers. The product of the chain reaction is a discreet nucleic acid duplex with termini corresponding to the ends of the specific primers employed.

Synthesis of Polynucleotides.

The oligonucleotide primers of the invention may be prepared using any suitable method, such as conventional phosphotriester and phosphodiester methods or automated embodiments thereof. In one such automated embodiment, diethylphosphoramidites are used as starting materials and may be synthesized as described by Beaucage, et al., Tetrahedron Letters, 22:1859-1862, (1981). One method for synthesizing oligonucleotides on a modified solid support is described in U.S. Pat. No. 4,458,066.

Oligonucleotides and polynucleotides can be prepared by standard synthetic techniques, e.g., using an automated DNA synthesizer. Methods for synthesizing oligonucleotides include well-known chemical processes, including, but not limited to, sequential addition of nucleotide phosphoramidites onto surface-derivatized particles, as described by T. Brown and Dorcas J. S. Brown in Oligonucleotides and Analogues A Practical Approach, F. Eckstein, editor, Oxford University Press, Oxford, pp. 1-24 (1991), and incorporated herein by reference.

An example of a synthetic procedure uses Expedite RNA phosphoramidites and thymidine phosphoramidite (Proligo, Germany). Synthetic oligonucleotides are deprotected and gel-purified (Elbashir et al. (2001) Genes & Dev. 15, 188-200), followed by Sep-Pak C18 cartridge (Waters, Milford, Mass., USA) purification (Tuschl et al. (1993) Biochemistry, 32:11658-11668). Other methods of oligonucleotide synthesis include, but are not limited to solid-phase oligonucleotide synthesis according to the phosphotriester and phosphodiester methods (Narang, et al., (1979) Meth. Enzymol. 68:90), and to the H-phosphonate method (Garegg, P. J., et al., (1985) "Formation of internucleotidic bonds via phosphonate intermediates", Chem. Scripta 25, 280-282; and Froehler, B. C., et al., (1986a) "Synthesis of DNA via deoxynucleoside H-phosphonate intermediates", Nucleic Acid Res., 14, 5399-5407, among others) and synthesis on a support (Beaucage, et al. (1981) Tetrahedron Letters 22:1859-1862) as well as phosphoramidate techniques (Caruthers, M. H., et al., "Methods in Enzymology," Vol. 154, pp. 287-314 (1988), U.S. Pat. Nos. 5,153,319, 5,132,418, 4,500,707, 4,458,066, 4,973,679, 4,668,777, and 4,415,732, and others described in "Synthesis and Applications of DNA and RNA," S. A. Narang, editor, Academic Press, New York, 1987, and the references contained therein, and nonphosphoramidite techniques. Solid phase synthesis helps isolate the oligonucleotide from impurities and excess reagents. Once cleaved from the solid support the oligonucleotide may be further isolated by known techniques.

Any nucleic acid specimen, in purified or nonpurified form, can be utilized as the starting nucleic acid(s), providing it contains, or is suspected of containing, the specific nucleic acid sequence containing the polymorphic locus. Thus, the process may amplify, for example, DNA or RNA, including messenger RNA, wherein DNA or RNA may be single stranded or double stranded. In the event that RNA is to be used as a template, enzymes, and/or conditions optimal for reverse transcribing the template to cDNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The specific nucleic acid sequence to be amplified, i.e., the polymorphic locus, may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA.

DNA utilized herein may be extracted from a body sample, tissue material and the like by a variety of techniques such as that described by Maniatis, et. al. in Molecular Cloning: A Laboratory Manual, Cold Spring Harbor, N.Y., p 280-281, 1982). If the extracted sample is impure, it may be treated before amplification with an amount of a reagent effective to open the cells, or animal cell membranes of the sample, and to expose and/or separate the strand(s) of the nucleic acid(s). This lysing and nucleic acid denaturing step to expose and separate the strands will allow amplification to occur much more readily.

The agent for DNA polymerization may be any compound or system which will function to accomplish the synthesis of primer extension products, including enzymes. Suitable enzymes for this purpose include, for example, polymerase muteins, reverse transcriptase, other enzymes, including heat-stable enzymes (i.e., those enzymes which perform primer extension after being subjected to temperatures sufficiently elevated to cause denaturation), such as Taq polymerase. The suitable enzyme will facilitate combination of the nucleotides in the proper manner to form the primer extension products which are complementary to each polymorphic locus nucleic acid strand. Generally, the synthesis will be initiated at the 3' end of each primer and proceed in the 5' direction along the template strand, until synthesis terminates, producing molecules of different lengths.

The amplification products may be detected by analyzing it by Southern blots without using radioactive probes. In such a process, for example, a small sample of DNA containing a very low level of the nucleic acid sequence of the polymorphic locus is amplified, and analyzed via a Southern blotting technique or similarly, using dot blot analysis. The use of non-radioactive probes or labels is facilitated by the high level of the amplified signal. Alternatively, probes used to detect the amplified products can be directly or indirectly detectably labeled, for example, with a radioisotope, a fluorescent compound, a bioluminescent compound, a chemiluminescent compound, a metal chelator or an enzyme. Those of ordinary skill in the art will know of other suitable labels for binding to the probe, or will be able to ascertain such, using routine experimentation. In the preferred embodiment, the amplification products are determinable by separating the mixture on an agarose gel containing ethidium bromide which causes DNA to be fluorescent.

Sequences amplified by the methods of the invention can be further evaluated, detected, cloned, sequenced, and the like, either in solution or after binding to a solid support, by any method usually applied to the detection of a specific DNA sequence such as PCR, oligomer restriction (Saiki, et. al., Bio/Technology, 3:1008-1012, (1985)), allele-specific oligonucleotide (ASO) probe analysis (Conner, et. al., Proc. Natl. Acad. Sci. U.S.A., 80:278, (1983)), oligonucleotide ligation assays (OLAs) (Landgren, et. al., Science, 241:1007, (1988)), and the like. Molecular techniques for DNA analysis have been reviewed (Landgren, et. al., Science, 242:229-237, (1988)).

Preferably, the method of amplifying is by PCR, as described herein and as is commonly used by those of ordinary skill in the art. Alternative methods of amplification have been described and can also be employed as long as the EGFR locus amplified by PCR using primers of the invention is similarly amplified by the alternative means. Such alternative amplification systems include but are not limited to self-sustained sequence replication, which begins with a short sequence of RNA of interest and a T7 promoter. The enzyme reverse transcriptase copies RNA into cDNA followed by degradation of the transcribed RNA. Another nucleic acid amplification technique is nucleic acid sequence-based amplification (NASBA) which uses reverse transcription and T7 RNA polymerase and incorporates two primers to target its cycling scheme. NASBA can begin with either DNA or RNA and finish with either, and amplifies to $10^8$ copies within 60 to 90 minutes. Alternatively, nucleic acid can be amplified by ligation activated transcription (LAT). LAT works from a single-stranded template with a single primer that is partially single-stranded and partially double-stranded Amplification is initiated by ligating a cDNA to the promoter oligonucleotide and within a few hours, amplification is $10^8$ to $10^9$ fold. The QB replicase system can be utilized by attaching an RNA sequence called MDV-1 to RNA complementary to a DNA sequence of interest. Upon mixing with a sample, the hybrid RNA finds its complement among the specimen's mRNAs and binds, activating the replicase to copy the tag-along sequence of interest. Another nucleic acid amplification technique, ligase chain reaction (LCR), works by using two differently labeled halves of a sequence of interest which are covalently bonded by ligase in the presence of the contiguous sequence in a sample, forming a new target. The repair chain reaction (RCR) nucleic acid amplification technique uses two complementary and target-specific oligonucleotide probe pairs, thermostable polymerase and ligase, and DNA nucleotides to geometrically amplify targeted sequences. A 2-base gap separates the oligonucleotide probe pairs, and the RCR fills and joins the gap, mimicking normal DNA repair. Nucleic acid amplification by strand displacement activation (SDA) utilizes a short primer containing a recognition site for Hinc II with short overhang on the 5' end which binds to target DNA. A DNA polymerase fills in the part of the primer opposite the overhang with sulfur-containing adenine analogs. Hinc II is added but only cuts the unmodified DNA strand. A DNA polymerase that lacks 5' exonuclease activity enters at the cite of the nick and begins to polymerize, displacing the initial primer strand downstream and building a new one which serves as more primer. SDA produces greater than 10.sup.7-fold amplification in 2 hours at 37 degree C. Unlike PCR and LCR, SDA does not require instrumented Temperature cycling. Another amplification system useful in the method of the invention is the QB Replicase System. Although PCR is the preferred method of amplification in the invention, these other methods can also be used to amplify the locus as described in the method of the invention.

A variety of methods well-known in the art can be used for detection of predetermined sequence variations by allele specific hybridization. Preferably, the test gene is probed with allele specific oligonucleotides (ASOs); and each ASO contains the sequence of a known mutation. ASO analysis detects specific sequence variations in a target polynucleotide fragment by testing the ability of a specific oligonucleotide probe to hybridize to the target polynucleotide fragment. Preferably, the oligonucleotide contains the mutant sequence (or its complement). The presence of a sequence variation in the target sequence is indicated by hybridization between the oligonucleotide probe and the target fragment under conditions in which an oligonucleotide probe containing a normal sequence does not hybridize to the target fragment. A lack of hybridization between the sequence variant (e.g., mutant) oligonucleotide probe and the target polynucleotide fragment indicates the absence of the specific sequence variation (e.g., mutation) in the target fragment. In a preferred embodiment, the test samples are probed in a standard dot blot format. Each region within the test gene that contains the sequence corresponding to the ASO is individually applied to a solid surface, for example, as an individual dot on a membrane. Each individual region can be produced, for example, as a separate PCR amplification product using methods well-known in the art (see, for example, the experimental embodiment set forth in Mullis, K. B., 1987, U.S. Pat. No. 4,683,202).

Membrane-based formats that can be used as alternatives to the dot blot format for performing ASO analysis include, but are not limited to, reverse dot blot, (multiplex amplification assay), and multiplex allele-specific diagnostic assay (MASDA).

In a reverse dot blot format, oligonucleotide or polynucleotide probes having known sequence are immobilized on the solid surface, and are subsequently hybridized with the labeled test polynucleotide sample. In this situation, the primers may be labeled or the NTPs maybe labeled prior to amplification to prepare a labeled test polynucleotide sample. Alternatively, the test polynucleotide sample may be labeled subsequent to isolation and/or synthesis In a multiplex format, individual samples contain multiple target sequences within the test gene, instead of just a single target sequence. For example, multiple PCR products each containing at least one of the ASO target sequences are applied within the same sample dot. Multiple PCR products can be produced simultaneously in a single amplification reaction using the methods of Caskey et al., U.S. Pat. No. 5,582,989. The same blot, therefore, can be probed by each ASO whose corresponding sequence is represented in the sample dots.

A MASDA format expands the level of complexity of the multiplex format by using multiple ASOs to probe each blot (containing dots with multiple target sequences). This procedure is described in detail in U.S. Pat. No. 5,589,330 by A. P. Shuber, and in Michalowsky et al., American Journal of Human Genetics, 59(4): A272, poster 1573 (October 1996), each of which is incorporated herein by reference in its entirety. First, hybridization between the multiple ASO probe and immobilized sample is detected. This method relies on the prediction that the presence of a mutation among the multiple target sequences in a given dot is sufficiently rare that any positive hybridization signal results from a single ASO within the probe mixture hybridizing with the corresponding mutant target. The hybridizing ASO is then identified by isolating it from the site of hybridization and determining its nucleotide sequence.

Designing an Allele Specific Oligonucleotide (ASO) Probe

An allele specific oligonucleotide probe is a short, single stranded polynucleotide that is engineered to hybridize exactly to a target sequence under a given set of conditions. Routinely, ASO probes are designed to contain sequences identical to the normal allele and sequence variation respectively. Hybridization of the probe to the target allows for the discrimination of a variant sample. Under stringent conditions, a probe with a variation as simple as a single-base pair will not hybridize to a normal sequence due to a destabilizing effect of the normal-mutant duplex (Ikuta, S. et al, Nucleic Acids Research, 15: 797-811 (1987).

The design of an ASO hybridization probe must meet two basic requirements. (Current Protocols in Human Genetics, section 9.4, (1995)). First, probes that are used together in the same pool should be around the same length. Although the standard length of a probe is optimally 17 base pairs, the range can be as short as about 14 or as long as about 27. If the mutation contains a long insertion, a longer probe may be desirable. Second, the mismatched region should not be placed at the end of the 17 base pair probe, but approximately in the middle of the sequence, approximately 5-7 bases from the 5' end of the probe. In addition, the placement of a mismatch, in the case of a longer probe, should not be at the end, but at a position that allows strong hybridization and stabilization of the polynucleotide strand. In order to minimize the effects of variations in base composition of the probes, tetramethylammonium chloride is used as in the ASO hybrid's buffer (Shuber, T., U.S. Pat. No. 5,633,134). Conventionally, ASO probes are synthesized on a DNA synthesizer. They can be labeled with isotopic or non-isotopic detection agents using means familiar to those of skill in the art. The process outlined in this application for making and using probes can be applicable for other gene sequences.

Suitable materials that can be used in the dot blot, reverse dot blot, multiplex, and MASDA formats are well-known in the art and include, but are not limited to nylon and nitrocellulose membranes.

When the target sequences are produced by PCR amplification, the starting material can be chromosomal DNA in which case the DNA is directly amplified. Alternatively, the starting material can be mRNA, in which case the mRNA is first reversed transcribed into cDNA and then amplified according to the well known technique of RT-PCR (see, for example, U.S. Pat. No. 5,561,058 by Gelfand et al.).

The methods described above are suitable for moderate screening of a limited number of sequence variations. However, with the need in molecular diagnosis for rapid, cost effective large scale screening, technologies have developed that integrate the basic concept of ASO, but far exceed the capacity for mutation detection and sample number. These alternative methods to the ones described above include, but are not limited to, large scale chip array sequence-based techniques. The use of large scale arrays allows for the rapid analysis of many sequence variants. A review of the differences in the application and development of chip arrays is covered by Southern, E. M., Trends In Genetics, 12: 110-115 (March 1996) and Cheng et al., Molecular Diagnosis, 1:183-200 (September 1996). Several approaches exist involving the manufacture of chip arrays. Differences include, but not restricted to: type of solid support to attach the immobilized oligonucleotides, labeling techniques for identification of variants and changes in the sequence-based techniques of the target polynucleotide to the probe.

A promising methodology for large scale analysis on 'DNA chips' is described in detail in Hacia et al., Nature Genetics, 14:441-447 (1996), which is hereby incorporated by reference in its entirety. As described in Hacia et al., high density arrays of over 96,000 oligonucleotides, each 20 nucleotides in length, are immobilized to a single glass or silicon chip using light directed chemical synthesis. Contingent on the number and design of the oligonucleotide probe, potentially every base in a sequence can be interrogated for alterations. Oligonucleotides applied to the chip, therefore, can contain sequence variations that are not yet known to occur in the population, or they can be limited to mutations that are known to occur in the population.

Prior to hybridization with oligonucleotide probes on the chip, the test sample is isolated, amplified and labeled (e.g. fluorescent markers) by means well known to those skilled in the art. The test polynucleotide sample is then hybridized to the immobilized oligonucleotides. The intensity of sequence-based techniques of the target polynucleotide to the immobilized probe is quantitated and compared to a reference sequence. The resulting genetic information can be used in molecular diagnosis.

In another embodiment of the invention, a method is provided for diagnosing the underlying cause for a subject having a relapse in cancer, or a relapse in lung cancer, comprising sequencing a target nucleic acid of a sample from a subject following amplification of the target nucleic acid. The EGFR gene, or fragments thereof, may be cloned and then sequenced to determine the presence of absence of a mutation. In such a situation, one need only compare the sequence obtained to a naturally occurring (wild type) EGFR gene, or portion thereof.

Other methods of DNA sequencing such as those of Sanger et al, Proc. Natl. Acad. Sci. USA, 74: 5463 (1977) or Maxam et al, Proc. Natl. Acad. Sci. USA, 74: 560 (1977) or other methods known in the art may be used.

In another embodiment of the invention a method is provided for diagnosing the underlying cause for a subject having a relapse in cancer comprising contacting a target nucleic acid of a sample from a subject with a reagent that detects the presence of the mutation of the present invention and detecting the mutation.

Another method comprises contacting a target nucleic acid of a sample from a subject with a reagent that detects the presence of the mutation and detecting the mutation. A number of hybridization methods are well known to those skilled in the art. Many of them are useful in carrying out the invention.

The materials for use in the method of the invention are ideally suited for the preparation of a diagnostic kit. Such a kit may comprise a carrier means being compartmentalized to receive in close confinement one or more container means such as vials, tubes, and the like, each of the container means comprising one or more of the separate elements to be used in the method. For example, one of the container means may comprise means for amplifying EGFR DNA, or a fragment thereof, said means comprising the necessary enzyme(s) and oligonucleotide primers for amplifying said target DNA from the subject. Another container may contain oligonucleotide probes for detecting the presence or absence of a mutation. Alternatively, another container may contain a restriction enzyme that recognizes the mutant sequence but not the wild type, or vice versa.

Other methods can include contacting a cancer tissue sample from a cancer patient with an antibody that specifically detects the EGFR T790M form of the EGFR protein but not the EFGR protein not containing this mutation. Alternatively a protein extract from a cancer tissue sample from a cancer patient can be obtained and analyzed by western blot, ELISA, or other protein detection techniques, for the presence or absence of the EGFR T790M mutant using an antibody specific to detect this mutation and not the EGFR protein not containing this mutation. The antibody to detect EGFR T790M mutant can be an antibody obtained from a hybridoma. A typical procedure for making hybridomas is as follows: (a) immunize mice with a certain immunogen; (b) remove the spleens from the immunized mice and make a spleen suspension in an appropriate medium; (c) fuse the suspended spleen cells with mouse myeloma cells; (d) dilute and culture the mixture of unfused spleen cells, unfused myeloma cells and fused cells in a selective medium which will not support growth of the unfused myeloma cells or spleen cells; (e) evaluate the supernatant in each container containing hybridoma for the presence of antibody to the immunogen; and (f) select and clone hybridomas producing the desired antibodies. Once the desired hybridoma has been selected and cloned, the resultant antibody is produced by in vitro culturing of the desired hybridoma in a suitable medium. As an alternative method, the desired hybridoma can be injected directly into mice to yield concentrated amounts of antibody [Kennett, et al., (1981) Ed., Monoclonal Antibodies. Hybridomas: A new dimension in biological analyses, Plenum Press, New York]. Hybridomas produced by fusion of murine spleen cells and murine myeloma cells have been described in the literature by Kohler et al., in Eur. J. Immunol. 6, 511-519 (1976); by Milstein et al. in Nature, 266, 550 (1977); and by Walsh, Nature, 266, 550 (1977); and by Walsh, Nature, 266, 495 (1977). The technique is also set out in some detail by Herzenberg and Milstein, in Handbook on Experimental Immunology, ed. Weir (Blackwell Scientific, London), 1979, pages 25.1 to 25.7 as well as in Kennett et al., supra. Patents relating to monoclonal antibodies against human tumors produced by hybridoma technology include U.S. Pat. Nos. 4,182,124 and 4,196,265. Representative of the art concerning monoclonal antibodies that have specificity for antigens on carcinoma cells are U.S. Pat. No. 4,350,683.

Specific mutations in the tyrosine kinase domain of EGFR are associated with sensitivity to either gefitinib or erlotinib, but mechanisms of acquired resistance have not yet been reported. Based upon analogous studies in other diseases with another kinase inhibitor, imatinib, a single amino acid substitution from threonine to methionine at position 790 in the wild-type EGFR kinase domain was predicted to lead to drug resistance, even before the association of exon 19 and 21 mutations of EGFR with drug responsiveness in NSCLC was reported. The C to T transition replacing Thr-766 with methionine (ACG to ATG) mutation was shown in vitro in the context of wild-type EGFR to confer resistance to gefitinib [21] and a related quinazoline inhibitor, PD153035 [22].

EXAMPLES

Materials and Methods

Tissue Procurement

Tumor specimens, including paraffin blocks, fine needle biopsies, and pleural effusions, were obtained through protocols approved by the Institutional Review Board of Memorial Sloan-Kettering Cancer Center (protocol 92-055 [7] and protocol 04-103 [Protocol S1]). All patients provided informed consent.

Mutational Analyses of EGFR and KRAS in Lung Tumors

Genomic DNA was extracted from tumor specimens, and primers for EGFR (exons 18-24) and KRAS2 (exon 2) analyses were as published [3,7]. All sequencing reactions were performed in both forward and reverse directions, and all mutations were confirmed at least twice from independent PCR isolates.

The exon 20 mutation (T790M) was also detected by length analysis of fluorescently labeled (FAM) PCR products on a capillary electrophoresis device (ABI 3100 Avant, Applied Biosystems, Foster City, Calif., United States), based on a new NlaIII restriction site created by the T790M mutation (2369 C→T). The following primers were used:
EGFR Ex20F, 5'-FAM-CTCCCTCCAGGAAGC-CTACGTGAT-3' (SEQ ID NO:4) and
EGFR Ex20R 5'-TTTGCGATCTGCACACACCA-3' (SEQ ID NO:5). Using serially mixed dilutions of DNA from NSCLC cell lines (H1975, L858R- and T790M-positive; H-2030, EGFR wild-type) for calibration, this assay detects the presence of the T790M mutation when H1975 DNA comprises 3% or more of the total DNA tested, compared to a sensitivity of 6% for direct sequencing (data not shown), with the caveat that the allele containing the T790M mutation is amplified about 2-fold in H1975 cells.

RT-PCR

The following primers were used to generate EGFR cDNA fragments spanning exon 20:
EGFR 2095F 5'-CCCAACCAAGCTCTCTTGAG-3' (SEQ ID NO:6) and
EGFR 2943R 5'-ATGACAAGGTAGCGCTGGGGG-3' (SEQ ID NO:7). The sequences targeted by EGFR 2095F and EGFR 2943R are shown underlined in Table 1. PCR products were ligated into plasmids using the TOPO TA-cloning kit (Invitrogen, Carlsbad, Calif., United States), as per manufacturer's instructions Minipreps of DNA from individual clones were sequenced using the T7 priming site of the cloning vector.

Functional Analyses of Mutant EGFRs

Mutations were introduced into full-length wild-type and mutant EGFR cDNAs using a QuikChange Site-Directed Mutagenesis Kit (Stratagene, La Jolla, Calif., United States) and cloned into expression vectors as described [3]. The following primers were used to generate the deletion (del) L747–E749;A750P mutant:
forward 5'-TAAAATTCCCGTCGCTATCAAGGAGC-CAACATCTCCGAAA GCCAACAAGG-3' (SEQ ID NO:8) and
reverse 5'-CCTTGTTGGCTTTCGGAGATGTTGGCTC-CTTGATAGCGACG GGAATTTTA-3' (SEQ ID NO:9). The following primers were used to introduce the T790M mutation:
forward 5'-AGCTCATCATGCAGCTCAT-3' (SEQ ID NO:10) and
reverse 5'-ATGAGCTGCATGATGAGCT-3' (SEQ ID NO:11). The L858R mutant cDNA was generated previously [3]. All mutant clones were fully re-sequenced bidirectionally to ensure that no additional mutations were introduced. Various EGFRs were transiently expressed in 293T human embryonic kidney cells as published [3]. Cells were treated with different concentrations of gefitinib or erlotinib.

Immunoblotting

See methods and supplementary methods in [3] for details on cell lysis, immunoblotting, and antibody reagents. At least three independent experiments were performed for all analyses.

Cell Culture

The NSCLC cell lines H1650, H1975, H2030, H2347, H2444, H358, and H1734 were purchased from American Type Culture Collection (Manassas, Va., United States). H3255 was a gift of B. Johnson and P. Janne. Cells were grown in complete growth medium (RPMI-1640; American Type Culture Collection catalog no. 30-2001) supplemented with 10% fetal calf serum, 10 units/ml penicillin, and 10 µg/ml streptomycin) at 37° C. and 5% $CO_2$. For viability studies, cells were seeded in complete growth medium in black 96-well clear bottom VIEWPLATES (PerkinElmer, Wellesley, Mass., United States) at a density of 5,000 (H1975 and H2030) or 7,500 cells per well (H3255). Following overnight incubation, cells were grown for 24 h in the supplemented RPMI-1640 medium with 0.1% serum. Cells (in supplemented RPMI-1640 medium containing 0.1% serum) were then incubated for 48 h in the continued presence of gefitinib or erlotinib.

Viability Assay

Cell viability was assayed using Calcein AM (acetoxymethyl ester of Calcein, Molecular Probes, Eugene, Oreg., United States). Following incubation with gefitinib or erlotinib, monolayers were washed twice with PBS (containing calcium and magnesium) and incubated with 7.5 µmol Calcein AM in supplemented RPMI-1640 (no serum) for 30 min. Labeling medium was removed, and cells were washed three times with PBS. Calcein fluorescence (Ex, 485 nm; Em, 535 nM) was detected immediately using a VICTOR™ V multilabel plate reader (PerkinElmer). Three independent experiments were performed for each cell line; each experiment included four to eight replicates per condition.

Production of Anti-Mutant EGFR Monoclonal and Polyclonal Antibodies

A group of three Balb/c female mice (Charles River Breeding Laboratories, Wilmington, Mass.) are injected with 5 ug/dose of purified truncated EGFR protein or fragment thereof containing the T790M mutation in 100 ul Detox adjuvant (RIBI ImmunoChem Res Inc, Hamilton, Mo.) by intraperitoneal injection on days 0, 3, 7, 10, and 14. On day 17 the animals are sacrificed, their spleens are removed and the lymphocytes fused with the mouse myeloma line 653 using 50% polyethylene glycol 4000 by an established procedure (see U.S. Pat. Nos. 5,939,269, and 5,658,791 as incorporated herein by reference). The fused cells are plated into 96-well microtiter plates at a density of $2 \times 10^5$ cells/well followed by HAT selection on day 1 post-fusion. Immobilized hybridoma culture supernatants are then reacted with biotinylated EGFR T790M mutant. The wells positive for anti-EGFR antibodies are expanded for further study. These cultures remain stable when expanded and cell lines are cryopreserved. The parental cultures are isotyped and then assayed for their ability to capture and to specifically recognize EGFR T790M mutant.

Alternatively, polyclonal rabbit antisera is raised against purified mutant protein peptides Polyclonal antibodies against the EGFR T790M mutant are obtained by coupling such peptides to Keyhole Limpet Hemocyanin with 0.05% glutaraldehyde, emulsified in Freund's complete adjuvant and injected intradermally at several sites. The animals are boosted four and seven weeks later with coupled peptide emulsified in Freund's incomplete adjuvant and bled ten days after the last injection.

Antibodies prepared according to the above procedures are then used for identifying and/or diagnosing tumor cells (i.e. in ultrathin sections of cancer tissues) for expression of EGFR T790M mutation and/or for therapeutic approaches according to standard procedures known in the art, e.g., U.S. Pat. Nos. 5,601,989, 5,563,247, 5,610,276, and 5,405,941, as incorporated herein by way of reference. These same antibodies are used for monitoring expression of EGFR T790M mutant.

Example 1

To confirm the presence of the EGFR T790M mutation, an allele-specific oligonucleotide PCR based assay (Guo, Z., Liu, Q. & Smith, L. M. Enhanced discrimination of single nucleotide polymorphisms by artificial mismatch hybridization. Nat. Biotechnol. 15, 331-335 (1997)) is performed by amplifying the mutant allele using one base mismatch PCR primers containing one 3' end and a 3-nitropyrrole residue. PCR products are created with a 3' mutant allele specific primer

```
(5' CACCGTGCAGCTCATCAT 3'       (SEQ ID NO: 12)
or
5' CGAAGGGCATGAGCTGCG 3'        (SEQ ID NO: 13))
``` containing the complement to the mutant base at the 3' end and a 3-nitropyrrole residue upstream of the 3' end. The mutant allele specific primer is capable of amplifying mutant DNA derived from frozen or paraffin-embedded tumors, but is unable to produce a product from normal DNA. At the same time, a wild-type (WT) 3' primer

```
(5' CACCGTGCAGCTCATCAC 3'       (SEQ ID NO: 14)
or
5' CGAAGGGCATGAGCTGCA 3'        (SEQ ID NO: 15))
``` is able to amplify only normal wild-type DNA but not mutant DNA. These experiments show that the mutant allele is amplified in tumor samples, whereas it is not amplified in normal adjacent tissues.

Example 2

Clonal Origin of the EGFR T790M Mutation

When careful tumor microdissection is performed in attempt to increase the relative percentage of tumor cells in any given sample, the ratio of the T:C alleles increases proportionately. The PCR is performed with one of the primers described in Example 1 and another primer amplifying in the contrary sense, so that a readily detectable fragment can be obtained for the EGFR sequence, either mutated or wild type, whose presence is being sought. The sequence of such primer can be easily designed by those of ordinary skill in the art. Results of such procedures demonstrate that the EGFR T790M mutation is clonal in origin.

Example 3

Assay for the EGFR T790M Mutation in Genomic DNA

A method is provided for detecting EGFR T790M mutation whereby a restriction enzyme MaHI is used to recognize the lack or presence of restriction site at the mutated codon. In this Example an assay is provided using a primer that spans the intron-exon boundary for exon 20. The fluorescence-based detection takes advantage of a PCR restriction fragment length polymorphism (PCR-RFLP) generated by the specific missense mutation. PCR amplification is performed with the exon-20-specific primers EGFR Ex20F (SEQ ID NO:4) and EGFR Ex20R (SEQ ID NO:5) (underlined in Table 4) spanning nucleotide 2369. Table 4 includes a portion (Seq ID No. 28) of the larger intron-exon 20-intron genomic sequence given in Table 3 (SEQ ID NO:3) from position 161904 to position 162970. The 3' terminus of the intron upstream from exon 20 is shown in bold type.

TABLE 4

. . . gtattttgaaactcaagatcgcattcatgcgtcttcacctggaagggggtccatgtgcccctccttc tggccaccatgcgaagccacactgacgtgcctctcc<u>ctccctccag</u>gaagcctacgtgatggccagcg tggacaacccccacgtgtgccgcctgctgggcatctgcctcacctccaccgtgcagctcatcacgcag ctcatgcccttcggctgcctcctggactatgtccgggaacacaaagacaatattggctcccagtacct gctcaac<u>tggtgtgtgcagatcgcaaagg</u> . . .

The wild-type sequence contains specific NlaIII sites, which upon digestion yield a 106-bp product (see Methods; FIG. 3A). Presence of the mutant 2369 T nucleotide creates a new NlaIII restriction digest site, yielding a slightly shorter product (97 bp; FIG. 3A), which is readily detected by fluorescent capillary electrophoresis. This test is about 2-fold more sensitive than direct sequencing. Any equivalent means that cleaves one of the 2369 alleles (wild type or mutant) but not the other is contemplated to be useful in this labeled fragment-length assay. The assay requires use of any known method of incorporating a label into the PCR amplicon such that resulting fragments are detectable.

Example 4

Case Reports

We identified secondary EGFR mutations in three of six individuals whose disease progressed on either gefitinib or erlotinib (Table 5). Brief case histories of these three patients are presented below.

Patient 1.

Figure 4:
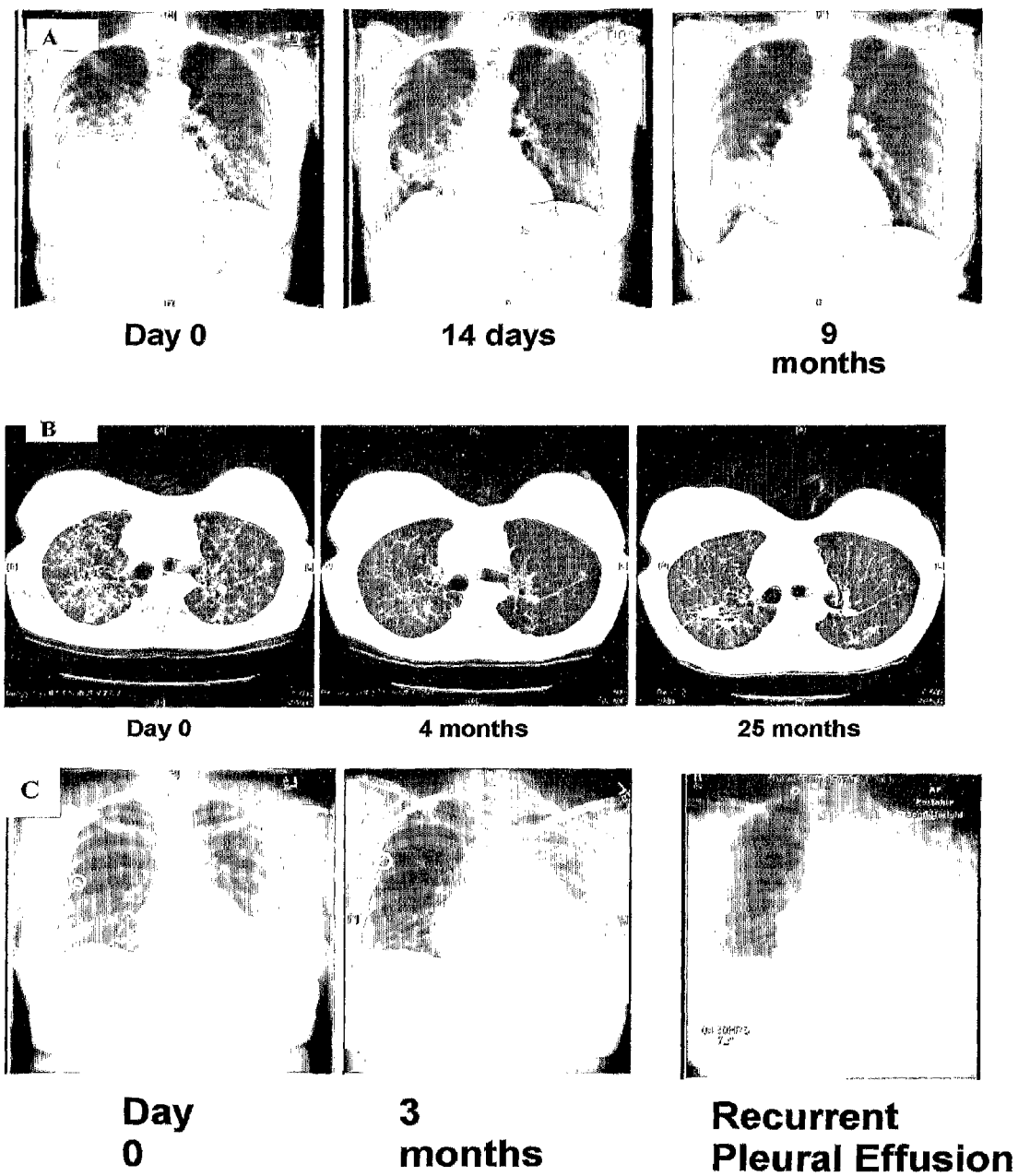
FIG. 4. Imaging Studies from Patients 1, 2, and 3
- (A) Patient 1. Serial chest radiographs from before (day 0) and during gefitinib treatment (14 d and 9 mo), demonstrating initial response and subsequent progression.
- (B) Patient 2. Serial CT studies of the chest before (day 0) and during erlotinib treatment (4 mo and 25 mo), demonstrating initial response and subsequent progression.
- (C) Patient 3. Serial chest radiographs before (day 0) and during adjuvant gefitinib treatment (3 mo), following complete resection of grossly visible disease. The left-sided pleural effusion seen at 3 mo recurred 4 mo later, at which time fluid was collected for molecular analysis.
Figure 5:
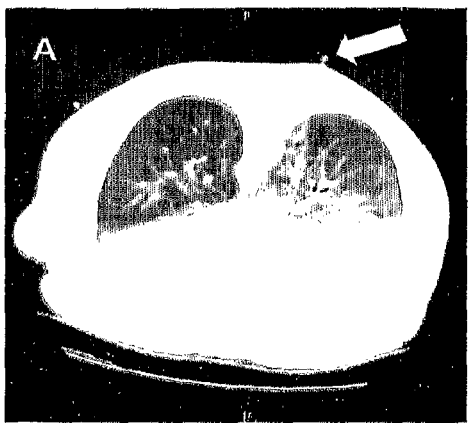
FIG. 5. Re-Biopsy Studies The biopsy needles are indicated by white arrows.
- (A) Patient 1. CT-guided biopsy of progressing lung lesions after 10 months on gefitinib (left panel). Two months later, fluid from a right-sided pleural effusion (right panel) was collected for molecular analysis.
Figure 5:
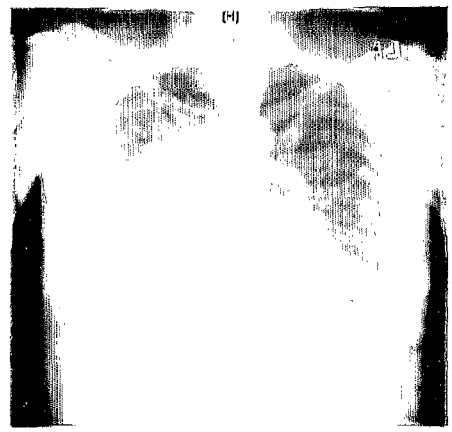
Figure 5:
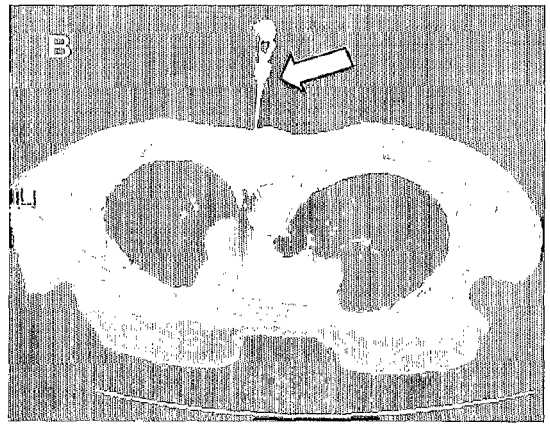
Figure 5:
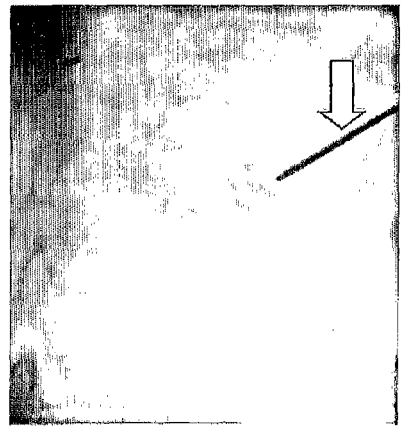

This 63-y-old female "never smoker" (smoked less than 100 cigarettes in her lifetime) initially presented with bilateral diffuse chest opacities and a right-sided pleural effusion. Transbronchial biopsy revealed adenocarcinoma. Disease progressed on two cycles of systemic chemotherapy, after which gefitinib, 250 mg daily, was started. Comparison of chest radiographs obtained prior to starting gefitinib (FIG. 4A, left panel) and 2 wk later (FIG. 4A, middle panel) showed dramatic improvement. Nine mo later, a chest radiograph revealed progression of disease (FIG. 4A, right panel). Subsequently, the patient underwent a computed tomography (CT)-guided biopsy of an area in the right lung base (FIG. 5A, left panel). Despite continued treatment with gefitinib, either with chemotherapy or at 500 mg daily, the pleural effusion recurred, 12 mo after initiating gefitinib (FIG. 5A, right panel). Pleural fluid was obtained for molecular studies. In total, this patient had three tumor specimens available for analysis: the original lung tumor biopsy, a biopsy of the progressing lung lesion, and pleural fluid. However, re-review of the original transbronchial biopsy showed that it had scant tumor cells (Table 5).

Patient 2.

This 55-y-old woman with a nine pack-year history of smoking underwent two surgical resections within 2 y (right lower and left upper lobectomies) for bronchioloalveolar carcinoma with focal invasion. Two years later, her disease recurred with bilateral pulmonary nodules and further progressed on systemic chemotherapy. Thereafter, the patient began erlotinib, 150 mg daily. A baseline CT scan of the chest demonstrated innumerable bilateral nodules (FIG. 4B, left panel), which were markedly reduced in number and size 4 mo after treatment (FIG. 4B, middle panel). After 14 mo of therapy, the patient's dose of erlotinib was decreased to 100 mg daily owing to fatigue. At 23 mo of treatment with erlotinib, a CT scan demonstrated an enlarging sclerotic lesion in the thoracic spine. The patient underwent CT-guided biopsy of this lesion (FIG. 5B, left panel), and the erlotinib dose was increased to 150 mg daily. After 25 mo of treatment, the disease progressed within the lung (FIG. 4B, right panel). Erlotinib was discontinued, and a fluoroscopically guided core needle biopsy was performed at a site of progressive disease in the lung (FIG. 5B, right panel). In total, this patient had three tumor specimens available for analysis: the original resected lung tumor, the biopsy of the enlarging spinal lesion, and the biopsy of the progressing lung lesion (Table 5).

Patient 3.

This 55-y-old female "never smoker" was treated for nearly 4.5 y with weekly paclitaxel and trastuzumab [17] for adenocarcinoma with bronchioloalveolar carcinoma features involving her left lower lobe, pleura, and mediastinal lymph nodes. Treatment was discontinued owing to fatigue. Subsequently, the patient underwent surgical resection. Because of metastatic involvement of multiple mediastinal lymph nodes and clinical features known at that time to be predictive of response to gefitinib (female, never smoker, bronchioloalveolar variant histology), she was placed on "adjuvant" gefitinib 1 mo later (FIG. 4C, left panel). This drug was discontinued after three mo when she developed a new left-sided malignant pleural effusion (FIG. 4C, middle panel). Despite drainage and systemic chemotherapy, the pleural effusion recurred 4 mo later (FIG. 4C, right panel), at which time pleural fluid was collected for analysis. In total, this patient had two clinical specimens available for analysis: tumor from the surgical resection and pleural fluid (Table 5).

TABLE 5

Specimens Analyzed in This Study for Mutations in the EGFR Tyrosine Kinase Domain (Exons 18 to 24) and KRAS (Exon 2)

| Patient | Pathology Specimen Analyzed | Date Obtained | Percent Tumor Cells | EGFR | KRAS |
|---|---|---|---|---|---|
| 1 | Transbronchial biopsy | Day 0 | Scant | Wild-type | Wild-type |
|   | Progressing lung lesion | 12 mo | >85% | L858R + T790M | Wild-type |
|   | Pleural effusion | 14 mo | >85% | L858R + T790M | Wild-type |
| 2 | Original lung lesion | Day 0 | >85% | del L747-E749; A750P | Wild-type |
|   | Progressing spine lesion | 75 mo | >85% | del L747-E749; A750P + T790M | Wild-type |
|   | Progressing lung lesion | 77 mo | >85% | del L747-E749; A750P + T790M | Wild-type |

TABLE 5-continued

Specimens Analyzed in This Study for Mutations in the EGFR Tyrosine Kinase Domain (Exons 18 to 24) and KRAS (Exon 2)

| Patient | Pathology Specimen Analyzed | Date Obtained | Percent Tumor Cells | EGFR | KRAS |
|---|---|---|---|---|---|
| 3 | Original pleural biopsy | Day 0 | n/a | Unavailable | Unavailable |
|  | Re-resection lung lesion | 68 mo | >85% | del E746-A750 | Wild-type |
|  | Pleural effusion | 76 mo | >50% | del E746-A750 + T790M | Wild-type |

The transbronchial biopsy in patient 1 had scant tumor cells; sequencing analysis revealed only wild-type sequence (see text). In three other cases, neither additional EGFR nor KRAS mutations were identified (data not shown).
Percent tumor cells: defined by assessment of corresponding histopathological slides.
del: deletion;
n/a—not applicable.

Example 5

Figure 6A:
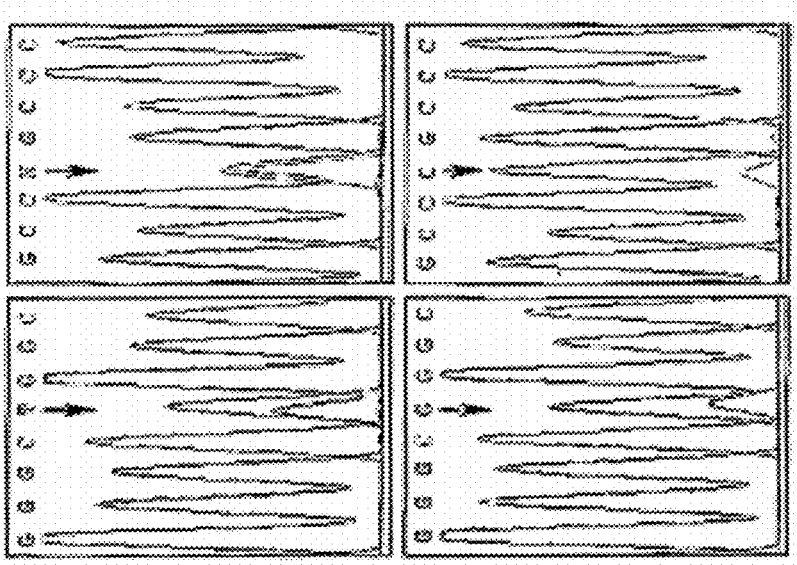

Patients' Tumors Contain EGFR Tyrosine Kinase Domain Mutations Associated with Sensitivity to EGFR Tyrosine Kinase Inhibitors We screened all available tumor samples from the three patients described in Example 4 for previously described drug-sensitive EGFR mutations, by direct DNA sequencing of exons 19 and 21 [3]. Tumor samples from patient 1 showed a T change at nucleotide 2573, resulting in the exon 21 L858R amino acid substitution commonly observed in drug-responsive tumors. This mutation was present in the biopsy material from the progressing lung lesion (FIG. 6A, upper panels; Table 5) and from cells from the pleural effusion (FIG. 6A, lower panels; Table 5), both of which on cytopathologic examination consisted of a majority of tumor cells (Table 5). Interestingly, comparisons of the tracings suggest that an increase in copy number of the mutant allele may have occurred. Specifically, while the ratio of wild-type (nucleotide T) to mutant (nucleotide G) peaks at position 2573 was approximately 1:1 or 1:2 in the lung biopsy specimen (FIG. 6A, upper panels), the pleural fluid cells demonstrated a dominant mutant G peak (FIG. 6A, lower panels). Consistent with this, a single nucleotide polymorphism (SNP) noted at nucleotide 2361 (A or G) demonstrated a corresponding change in the ratios of A:G, with a 1:1 ratio in the transbronchial biopsy, and a nearly 5:1 ratio in the pleural fluid (FIG. 7A). Notably, we did not detect the 2573 T→G mutation in the original transbronchial biopsy specimen (Table 5; data not shown). As stated above, this latter specimen contained scant tumor cells, most likely fewer than needed for detection of an EGFR mutation by direct sequencing (see [7]).

Figure 6B:
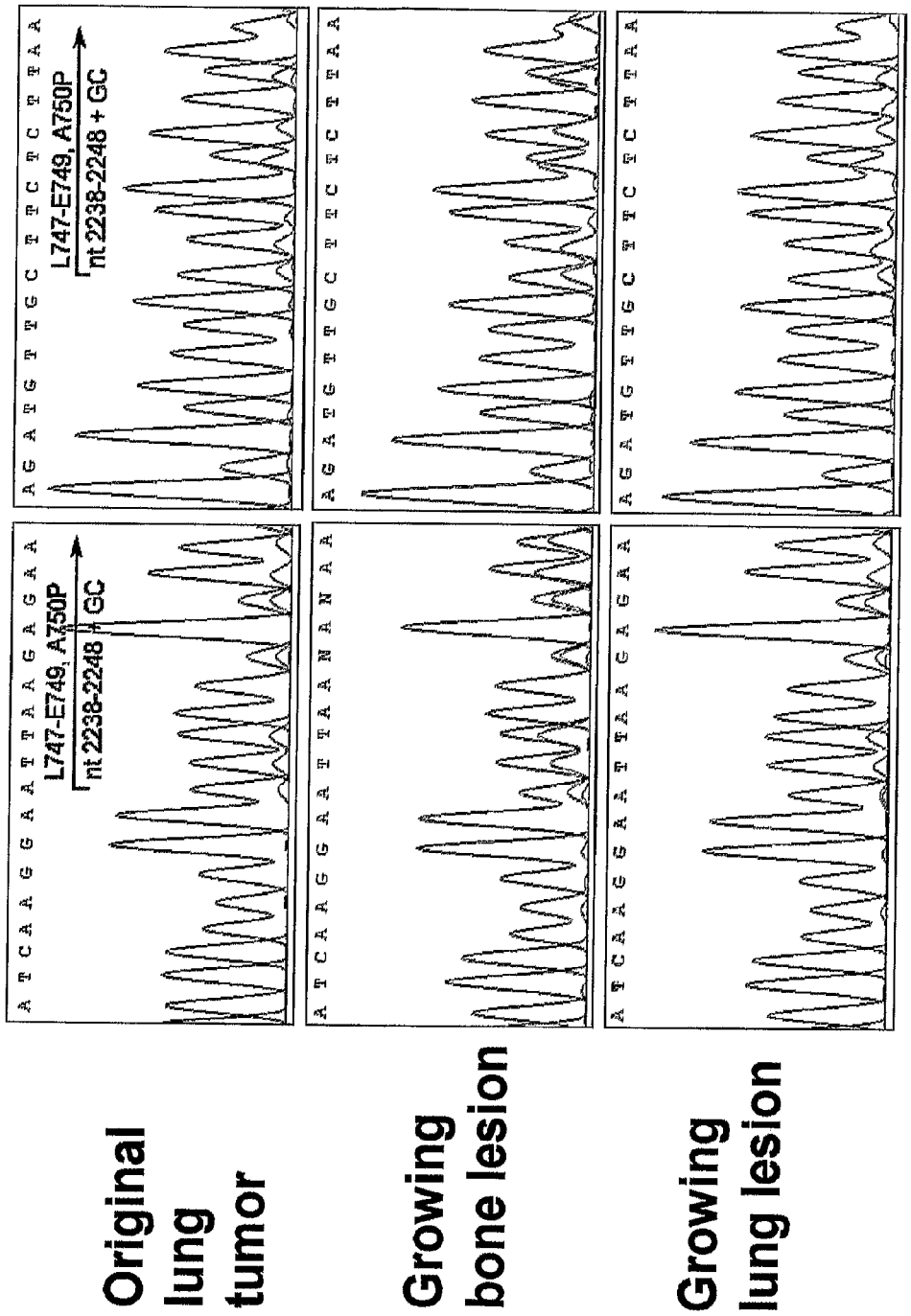

All three specimens from patient 2, including the original lung tumor and the two metastatic samples from bone and lung, showed an exon 19 deletion involving elimination of 11 nucleotides (2238-2248) and insertion of two nucleotides, G and C (FIG. 6B, all panels; Table 5). These nucleotide changes delete amino acids L747-E749 and change amino acid 750 from alanine to proline (A750P). A del L747-E749; A750P mutation was previously reported with different nucleotide changes [2]. In all samples from patient 2, the wild-type sequence predominated at a ratio of about 3:1 over the mutant sequence.

Both of the available tumor samples from patient 3 contained a deletion of 15 nucleotides (2236-2250) in exon 19 (Table 5; data not shown), resulting in elimination of five amino acids (del E746-A750). This specific deletion has been previously reported [3]. The ratio of mutant to wild-type peaks was approximately 1:1 in both specimens (data not shown).

Collectively, these results demonstrate that tumors from all three patients contain EGFR mutations associated with sensitivity to the tyrosine kinase inhibitors gefitinib and erlotinib. In addition, these data show that within individual patients, metastatic or recurrent lesions to the spine, lung, and pleural fluid contain the same mutations. These latter observations support the idea that relapsing and metastatic tumor cells within individuals are derived from original progenitor clones.

Example 6

A Secondary Missense Mutation in the EGFR Kinase Domain Detected in Lesions that Progressed while on Treatment with Either Gefitinib or Erlotinib To determine whether additional mutations in the EGFR kinase domain were associated with progression of disease in these patients, we performed direct sequencing of all of the exons (18 through 24) encoding the EGFR catalytic region in the available tumor specimens.

Analysis of patient 1's pre-gefitinib specimen, which contained scant tumor cells (Table 5; see above), not surprisingly showed only wild-type EGFR sequence (Table 5; data not shown). However, careful analysis of the exon 20 sequence chromatograms in both forward and reverse directions from this patient's lung biopsy specimen obtained after disease progression on gefitinib demonstrated an additional small peak at nucleotide 2369, suggesting a C→T mutation (FIG. 7A, upper panels; Table 5). This nucleotide change leads to substitution of methionine for threonine at position 790 (T790M). The 2369 C→T mutant peak was even more prominent in cells from the patient's pleural fluid, which was obtained after further disease progression on gefitinib (FIG. 7A, lower panels; Table 5). The increase in the ratio of mutant to wild-type peaks obtained from analyses of the lung specimen and pleural fluid paralleled the increase in the ratio of the mutant G peak (leading to the L858R mutation) to the wild-type T peak at nucleotide 2573 (see above; FIG. 6A), as well as the increase in the ratio of the A:G SNP at position 2361 (FIG. 7A). Collectively, these findings imply that the exon 20 T790M mutation was present on the same allele as the exon 21 L858R mutation, and that a subclone of cells harboring these mutations emerged during drug treatment.

In patient 2, the tumor-rich sample obtained prior to treatment with erlotinib did not contain any additional mutations in the exons encoding the EGFR tyrosine kinase domain (FIG. 7B, upper panels; Table 5). By contrast, her progressing bone and lung lesions contained an additional small peak at nucleotide 2369, suggesting the existence of a subclone of tumor cells with the same C→T mutation observed in patient 1 (FIG. 7B, middle and lower panels; Table 5). The relative sizes of the 2369 T mutant peaks seen in these latter two samples appeared to correlate with the relative size of the corresponding peaks of the exon 19 deletion (FIG. 6B). Interestingly, the SNP at nucleotide 2361 (A or G) was detected in specimens from patient 2 before but not after treatment with erlotinib, suggesting that one EGFR allele underwent amplification or deletion during the course of treatment (FIG. 6B).

Patient 3 showed results analogous to those of patient 2. A tumor-rich pre-treatment specimen did not demonstrate EGFR mutations other than the del E746-A750 exon 19 deletion; specifically, in exon 20, no secondary changes were detected (FIG. 7C, upper panels; Table 5). However, analysis of DNA from cells in the pleural effusion that developed after treatment with gefitinib showed the C→T mutation at nucleotide 2369 in exon 20 (FIG. 7C, lower panels; Table 5), corresponding to the T790M mutation described above. There was no dramatic change between the two samples in the ratio of the A:G SNP at position 2361. The mutant 2369 T peak was small, possibly because gefitinib had been discontinued in this patient for 4 mo at the time pleural fluid tumor cells were collected; thus, there was no selective advantage conferred upon cells bearing the T790M mutation.

To determine whether the 2369 C→T mutation was a previously overlooked EGFR mutation found in NSCLCs, we re-reviewed exon 20 sequence tracings derived from analysis of 96 fresh-frozen resected tumors [3] and 59 paraffin-embedded tumors [7], all of which were removed from patients prior to treatment with an EGFR tyrosine kinase inhibitor. We did not detect any evidence of the T790M mutation in these 155 tumors (data not shown). Collectively, our results suggest that the T790M mutation is associated with lesions that progress while on gefitinib or erlotinib. Moreover, at least in patients 1 and 2, the subclones of tumor cells bearing this mutation probably emerged between the time of initial treatment with a tyrosine kinase inhibitor and the appearance of drug resistance.

Additionally, after the initial characterization of the three patients with the T790M mutation described above in more detail, four other patients were found to have the T790M mutation after developing resistance to Iressa or Tarceva out of a total of 13 patients that initially responded and then relapsed while on the treatment. Table 6 summarizes the results (the table does not include data from the patient that never responded to treatment and that was later found to have T790M):

TABLE 6

| Pt | Drug | Months | Site | Time of biopsy | 1ry Mutation | 2ry Mutation |
|---|---|---|---|---|---|---|
| 1 | E | 19 | Spine/lung | 26 | del | T790M |
| 2 | G | 10 | Pl fluid | 10 | del | T790M |
| 3 | G | 13 | Lung | 14 | del | T790M |
| 4 | G | 11 | Omentum | 12 | del | T790M |
| 5 | G | 15 | Lung/peric fl | 16 | del | T790M |
| 6 | G | 15 | Lung | 16 | L858R | T790M |
| 7 | E | 16 | Lung | 22 | del | none |
| 8 | G | 11 | Lung | 13 | del | none |
| 9 | G | 11 | Pl fluid/ascites | 12 | del | none |
| 10 | G | 19 | Ascites | 23 | del | none |

TABLE 6-continued

| Pt | Drug | Months | Site | Time of biopsy | 1ry Mutation | 2ry Mutation |
|---|---|---|---|---|---|---|
| 11 | G | 7 | Cervix | 8 | del | none |
| 12 | G | 12 | Ing LN | 16 | del | none |
| 13 | G | 7 | Pleura | 9 | del | none |

In seven patients (case histories not described here) with lung adenocarcinomas who improved but subsequently progressed on therapy with either gefitinib or erlotinib, we examined DNA from tumor specimens obtained during disease progression. In all seven patients, we found EGFR mutations associated with drug sensitivity (all exon 19 deletions). However, we did not find any additional mutations in exons 18 to 24 of EGFR, including the C→T change at position 2369 (data not shown). These results imply that alternative mechanisms of acquired drug resistance exist.

Example 7

Patients' Progressive Tumors Lack KRAS Mutations

Mutations in exon 2 of KRAS2 occur in about one-fourth of NSCLCs. Such mutations rarely, if ever, accompany EGFR mutations and are associated with primary resistance to gefitinib or erlotinib [7]. To evaluate the possibility that secondary KRAS mutations confer acquired resistance to these drugs, we performed mutational profiling of KRAS2 exon 2 from tumor specimens from patients 1 to 3, as well as the three additional patients lacking evidence of the T790M mutation. None of the specimens contained any changes in KRAS (Table 5; and data not shown), indicating that KRAS mutations were not responsible for drug resistance and tumor progression in these six patients.

Example 8

An Established NSCLC Cell Line Also Contains Both T790M and L858R Mutations

We profiled the EGFR tyrosine kinase domain (exons 18 to 24) and KRAS exon 2 in eight established NSCLC lines (Table 7). Surprisingly, one cell line—H1975—contained the same C→T mutation at position 2369 (T790M) as described above (FIG. 7D, lower panel). This cell line had previously been shown by others to contain a 2573 T→G mutation in exon 21 (L858R) [18], which we confirmed (FIG. 7D, upper panel); in addition, H1975 was reported to be more sensitive to gefitinib inhibition than other lung cancer cell lines bearing wild-type EGFR [18]. Only exons 19 and 21 were apparently examined in this published study.

TABLE 7

Status of NSCLC Cell Lines Analyzed for EGFR Tyrosine Kinase Domain (Exons 18 to 24) and KRAS (Exon 2) Mutations

| Cell Line | EGFR | KRAS |
|---|---|---|
| H1650 | del E746-A750 | Wild-type |
| H3255 | L858R | Wild-type |
| H1975 | L858R + T790M | Wild-type |
| H2030 | Wild-type | G12C |
| H358 | Wild-type | G12C |
| H2444 | Wild-type | G12V |
| H1734 | Wild-type | G13C |
| H2347 | Wild-type | L19F | del: deletion. See methods for further details.

In our own analysis of H1975 (exons 18 to 24), the mutant 2369 T peak resulting in the T790M amino acid substitution was dominant, suggesting an increase in copy number of the mutant allele in comparison to the wild-type allele. The ratio of mutant to wild-type peaks was similar to that of the mutant 2573 G (corresponding to the L858R amino acid substitution) to wild-type T peaks (FIG. 7D, all panels), implying that the T790M and L858R mutations were in the same amplified allele. To further investigate this possibility, we performed RT-PCR to generate cDNAs that spanned exon 20 of EGFR and included sequences from exon 19 and 21. PCR products were then cloned, and individual colonies were analyzed for EGFR mutations. Sequencing chromatograms of DNA from four of four clones showed both the 2369 C→T and 2573 T→G mutations, confirming that both mutations were in the same allele (data not shown).

Other NSCLC cell lines carried either EGFR or KRAS mutations, but none had both (Table 7). As reported, H3255 contained an L858R mutation [19] and H1650 contained an exon 19 deletion [18]. No other cell lines analyzed contained additional mutations in the exons encoding the EGFR tyrosine kinase domain.

Example 9

A Novel PCR Restriction Fragment Length Polymorphism Assay Independently Confirms the Absence or Presence of the T790M Mutation As stated above, the mutant peaks suggestive of a T790M mutation in exon 20 were small in some sequence chromatograms. To eliminate the possibility that these peaks were due to background "noise," we sought to confirm the presence of the 2369 C→T mutation in specific samples, by developing an independent test, based on a fluorescence detection assay that takes advantage of a PCR restriction fragment length polymorphism (PCR-RFLP) generated by the specific missense mutation. After PCR amplification with exon-20-specific primers spanning nucleotide 2369, wild-type sequence contains specific NlaIII sites, which upon digestion yield a 106-bp product (see Methods; FIG. 3A). Presence of the mutant 2369 T nucleotide creates a new NlaIII restriction digest site, yielding a slightly shorter product (97 bp), readily detected by fluorescent capillary electrophoresis. This test is about 2-fold more sensitive than direct sequencing (see Methods; data not shown).

We first used DNA from the H1975 cell line (which contains both T790M and L858R mutations) to confirm the specificity of the PCR-RFLP assay. As expected, analysis of these cells produced both the 97- and 106-bp fragments. By contrast, analysis of DNA from 112030 (which contains wild-type EGFR; Table 7) showed only the 106-bp fragment (FIG. 3A). These data show that this test can readily indicate the absence or presence of the mutant allele in DNA samples. However, this test was only semi-quantitative, as the ratio of the mutant 97-bp product versus the wild-type 106-bp product varied in independent experiments from approximately 1:1 to 2:1.

We next used this PCR-RFLP assay to assess various patient samples for the presence of the specific 2369 C→T mutation corresponding to the T790M amino acid substitution. DNA from the progressing bone and lung lesions in patient 1 produced both the 97- and 106-bp fragments, but DNA from the original lung tumor did not (FIG. 3B). The ratio of mutant to wild-type products was higher in the cells from the pleural fluid, consistent with the higher peaks seen on the chromatograms from direct sequencing of exon 20 (see FIG. 7A). Likewise, DNA from progressive lesions from patients 2 and 3 yielded both 97- and 106-bp fragments in the PCR-RFLP assay (FIG. 3B), whereas the pre-treatment specimens did not produce the 97-bp product. Collectively, these data from an independent assay confirm that the T790M mutation was present in progressing lesions from all three patients. We were also unable to detect the T790M mutation in any specimens from the three additional patients with acquired resistance that failed to demonstrate secondary mutations in EGFR exons 18 to 24 by direct sequencing (data not shown).

Example 10

Biochemical Properties of EGFR Mutants

To determine how the T790M mutation would affect EGFR proteins already containing mutations associated with sensitivity to EGFR tyrosine kinase inhibitors, we introduced the specific mutation into EGFR cDNAs that encoded the exon 21 and 19 mutations found in patients 1 and 2, respectively. Corresponding proteins ([i] L858R and L858R plus T790M, [ii] del L747–E749;A750P and del L747–E749;A750P plus T790M, and [iii] wild-type EGFR and wild-type EGFR plus T790M) were then produced by transient transfection with expression vectors in 293T cells, which have very low levels of endogenous EGFR [3]. Various lysates from cells that were serum-starved and pre-treated with gefitinib or erlotinib were analyzed by immunoblotting. Amounts of total EGFR (t-EGFR) were determined using an anti-EGFR monoclonal antibody, and actin served as an indicator of relative levels of protein per sample. To assess the drug sensitivity of the various EGFR kinases in surrogate assays, we used a Y1092-phosphate-specific antibody (i.e., phospho-EGFR [p-EGFR]) to measure the levels of "autophosphorylated" Tyr-1092 on EGFR in relation to levels of t-EGFR protein. We also assessed the global pattern and levels of induced tyrosine phosphorylation of cell proteins by using a generalized anti-phosphotyrosine reagent (RC-20).

Gefitinib inhibited the activity of wild-type and L858R EGFRs progressively with increasing concentrations of drug, as demonstrated by a reduction of tyrosine-phosphorylated proteins (FIG. 8A) and a decrease in p-EGFR:t-EGFR ratios (FIG. 8B). By contrast, wild-type and mutant EGFRs containing the T790M mutation did not display a significant change in either phosphotyrosine induction or p-EGFR:t-EGFR ratios (FIGS. 8A and 8B). Similar results were obtained using erlotinib against wild-type and del E747–L747;A750P EGFRs in comparison to the corresponding mutants containing the T790M mutation (FIG. 8C). These results suggest that the T790M mutation may impair the ability of gefitinib or erlotinib to inhibit EGFR tyrosine kinase activity, even in EGFR mutants (i.e., L858R or an exon 19 deletion) that are clinically associated with drug sensitivity.

Example 11

Resistance of a NSCLC Cell Line Harboring Both T790M and L858R Mutations to Gefitinib or Erlotinib To further explore the functional consequences of the T790M mutation, we determined the sensitivity of various NSCLC cells lines grown in the presence of either gefitinib or erlotinib, using an assay based upon Calcein AM. Uptake and retention of this fluorogenic esterase substrate by vehicleversus drug-treated live cells allows for a comparison of relative cell viability among cell lines [20]. The H3255 cell line, which harbors the L858R mutation and no other EGFR TK domain mutations (Table 7), was sensitive to treatment with gefitinib, with an $IC_{50}$ of about 0.01 µmol (FIG. 9). By contrast, the H1975 cell line, which contains both L858R and T790M mutations (Table 7), was approximately 100-fold less sensitive to drug, with an $IC_{50}$ of about 1 mol (FIG. 9). In fact, the sensitivity of H1975 cells was more similar to that of H2030, which contains wild-type EGFR (exons 18 to 24) and mutant KRAS (FIG. 9). Very similar results were obtained with erlotinib (FIG. 10).

Although the present invention may have been disclosed and illustrated herein by reference to exemplary embodiments thereof, all equivalent embodiments, including alterations, additions and omissions, are encompassed within the spirit and scope of the invention as disclosed in the specification and the claims.

REFERENCES

1. Lynch T J, Bell D W, Sordella R, Gurubhagavatula S, Okimoto R A, et al. (2004) Activating mutations in the epidermal growth factor receptor underlying responsiveness of non-small-cell lung cancer to gefitinib. N Engl J Med 350: 2129-2139.
2. Paez J G, Janne P A, Lee J C, Tracy S, Greulich H, et al. (2004) EGFR mutations in lung cancer: Correlation with clinical response to gefitinib therapy. Science 304: 1497-1500.
3. Pao W, Miller V, Zakowski M, Doherty J, Politi K, et al. (2004) EGF receptor gene mutations are common in lung cancers from "never smokers" and are associated with sensitivity of tumors to gefitinib and erlotinib. Proc Natl Acad Sci USA 101: 13306-13311.
4. Huang S F, Liu H P, Li L H, Ku Y C, Fu Y N, et al. (2004) High frequency of epidermal growth factor receptor mutations with complex patterns in non-small cell lung cancers related to gefitinib responsiveness in Taiwan. Clin Cancer Res 10: 8195-8203.
5. Kosaka T, Yatabe Y, Endoh H, Kuwano H, Takahashi T, et al. (2004) Mutations of the epidermal growth factor receptor gene in lung cancer: Biological and clinical implications. Cancer Res 64: 8919-8923.
6. Shigematsu H, Lin L, Takahashi T, Nomura M, Suzuki M, et al. (2004) Clinical and biological features of epidermal growth factor receptor mutations in lung cancers. J Natl Cancer Inst. In press.
7. Pao W, Wang T Y, Riely G J, Miller V A, Pan Q, et al. (2005) KRAS mutations and primary resistance of lung adenocarcinomas to gefitinib or erlotinib. PLoS Medicine 2: e17.
8. Deininger M, Buchdunger E, Druker B J (2004) The development of imatinib as a therapeutic agent for chronic myeloid leukemia. Blood: Epub ahead of print.
9. Al-Ali H K, Heinrich M C, Lange T, Krahl R, Mueller M, et al. (2004) High incidence of BCR-ABL kinase domain mutations and absence of mutations of the PDGFR and KIT activation loops in CML patients with secondary resistance to imatinib. Hematol J 5: 55-60.
10. Gone M E, Mohammed M, Ellwood K, Hsu N, Paquette R, et al. (2001) Clinical resistance to STI-571 cancer therapy caused by BCR-ABL gene mutation or amplification. Science 293: 876-880.
11. Shah N P, Nicoll J M, Nagar B, Gone M E, Paquette R L, et al. (2002) Multiple BCR-ABL kinase domain mutations confer polyclonal resistance to the tyrosine kinase inhibitor imatinib (STI571) in chronic phase and blast crisis chronic myeloid leukemia. Cancer Cell 2: 117-125.
12. O'Hare T, Pollock R, Stoffregen E P, Keats J A, Abdullah O M, et al. (2004) Inhibition of wild-type and mutant Bcr-Abl by AP23464, a potent ATP-based oncogenic protein kinase inhibitor: Implications for CML. Blood 104: 2532-2539.
13. Shah N P, Tran C, Lee F Y, Chen P, Norris D, et al. (2004) Overriding imatinib resistance with a novel ABL kinase inhibitor. Science 305: 399-401.
14. Sawyers C (2004) Targeted cancer therapy. Nature 432: 294-297.
15. Tamborini E, Bonadiman L, Greco A, Albertini V, Negri T, et al. (2004) A new mutation in the KIT ATP pocket causes acquired resistance to imatinib in a gastrointestinal stromal tumor patient. Gastroenterology 127: 294-299.
16. Cools J, DeAngelo D J, Gotlib J, Stover E H, Legare R D, et al. (2003) A tyrosine kinase created by fusion of the PDGFRA and FIP1L1 genes as a therapeutic target of imatinib in idiopathic hypereosinophilic syndrome. N Engl J Med 348: 1201-1214.
17. Krug L M, Miller V A, Crapanzano J, Ng K K, Pizzo B, et al. (2001) Randomized phase II trial of trastuzumab (tras) plus either weekly docetaxel (doc) or paclitaxel (pac) in previously untreated advanced non-small cell lung cancer (NSCLC). Proc Am Soc Clin Oncol 20: 1328.
18. Sordella R, Bell D W, Haber D A, Settleman J (2004) Gefitinib-sensitizing EGFR mutations in lung cancer activate anti-apoptotic pathways. Science 305: 1163-1167.
19. Tracy S, Mukohara T, Hansen M, Meyerson M, Johnson B E, et al. (2004) Gefitinib induces apoptosis in the EGFRL858R non-small cell lung cancer cell line H3255. Cancer Res 64: 7241-7244.
20. Bozyczko-Coyne D, McKenna B W, Connors T J, Neff N T (1993) A rapid fluorometric assay to measure neuronal survival in vitro. J Neuroscience Meth 50: 205-216.
21. Blencke S, Zech B, Engkvist O, Greff Z, Orfi L, et al. (2004) Characterization of a conserved structural determinant controlling protein kinase sensitivity to selective inhibitors. Chem Biol 11: 691-701.
22. Blencke S, Ullrich A, Daub H (2003) Mutation of threonine 766 in the epidermal growth factor receptor reveals a hotspot for resistance formation against selective tyrosine kinase inhibitors. J Biol Chem 278: 15435-15440.
23. Kreuzer K A, Le Coutre P, Landt O, Na I K, Schwarz M, et al. (2003) Preexistence and evolution of imatinib mesylate-resistant clones in chronic myelogenous leukemia detected by a PNA-based PCR clamping technique. Ann Hematol 82: 284-289.
24. Stamos J, Sliwkowski M X, Eigenbrot C (2002) Structure of the epidermal growth factor receptor kinase domain alone and in complex with a 4-anilinoquinazoline inhibitor. J Biol Chem 277: 46265-46272.
25. Daub H, Specht K, Ullrich A (2004) Strategies to overcome resistance to targeted protein kinase inhibitors. Nat Rev Drug Discov 3: 1001-1010.
26. Wood E R, Truesdale A T, McDonald O B, Yuan D, Hassell A, et al. (2004) A unique structure for epidermal growth factor receptor bound to GW572016 (Lapatinib): Relationships among protein conformation, inhibitor off-rate, and receptor activity in tumor cells. Cancer Res 64: 6652-6659.
27. Chen L L, Trent J C, Wu E F, Fuller G N, Ramdas L, et al. (2004) A missense mutation in KIT kinase domain 1 correlates with imatinib resistance in gastrointestinal stromal tumors. Cancer Res 64: 5913-5919.
28. Gone M E, Sawyers C L (2002) Molecular mechanisms of resistance to STI571 in chronic myeloid leukemia. Curr Opin Hematol 9: 303-307.

We claim:

1. A method for predicting development of acquired resistance to the therapeutic effects of an epidermal growth factor (EGFR) tyrosine kinase inhibitor in a patient that is suffering from a cancer, wherein the method comprises the steps of:
 (a) obtaining a sample from the patient, wherein the cancer harbors a somatic gain-of-function mutation in the tyrosine kinase domain of EGFR that enhances the sensitivity of the cancer to the tyrosine kinase inhibitor,
 (b) testing the sample to determine whether the gene encoding EGFR is present in a mutant form that encodes a T790M mutant of EGFR in addition to the somatic gain of function mutation, and
 (c) identifying the cancer as one that has become or will become resistant to the EGFR tyrosine kinase inhibitor if the T790M mutant form is present or as having continuing sensitivity to the EGFR tyrosine kinase inhibitor if the T790M mutant form is absent,
 wherein the testing of the sample in step (b) is performed by a method selected from the group consisting of:
  (i) performing PCR amplification using a pair of primers that flank the region encoding amino acid 790 of EGFR to form amplicons that include the bases encoding amino acid 790 of EGFR, and evaluating the amplicons to determine if a mutation is present that would result in a T790M mutation in EGFR;
  (ii) performing PCR amplification using a pair of primers, and evaluating the amplicons to determine if a mutation is present that would result in a T790M mutation in EGFR, and wherein one of the primers used in the PCR amplification step binds at a position that includes the bases encoding a T790M mutation in EGFR; and
  (iii) probing the sample with a probe oligonucleotide, wherein the probe binds preferentially to a 2369C→T mutant or a wild type EGFR sequence, and detecting binding of the probe.

2. The method of claim 1, wherein the patient is treated with the EGFR tyrosine kinase inhibitor prior to obtaining the sample from the patient.

3. The method of claim 2, wherein the patient is responsive to the EGFR tyrosine kinase inhibitor when it is first administered.

4. The method of claim 1, wherein the somatic gain-of-function mutation is L858R.

5. The method of claim 1, wherein the somatic gain-of-function mutation is a deletion of the amino acid sequence Leu-Arg-Glu-Ala from exon 19 of EGFR.

6. The method of claim 1, wherein the EGFR tyrosine kinase inhibitor is gefitinib or erlotinib.

7. The method of claim 6, wherein the patient is treated with the EGFR tyrosine kinase inhibitor prior to obtaining the sample from the patient.

8. The method of claim 6, wherein the somatic gain-of-function mutation is L858R.

9. The method of claim 6, wherein the somatic gain-of-function mutation is a deletion of the amino acid sequence Leu-Arg-Glu-Ala from exon 19 of EGFR.

10. The method of claim 6, wherein the somatic gain-of-function mutation is a deletion from exon 19 of EGFR.

11. The method of claim 1, wherein the cancer is non-small cell lung cancer.

12. The method of claim 7, wherein the patient is responsive to the EGFR tyrosine kinase inhibitor when it is first administered.

13. The method of claim 11, wherein the EGFR tyrosine kinase inhibitor is gefitinib or erlotinib.

14. The method of claim 1, wherein the step of testing the sample comprises the steps of: performing PCR amplification using a pair of primers that flank the region encoding amino acid 790 of EGFR to form amplicons that include the bases encoding amino acid 790 of EGFR, and evaluating the amplicons to determine if a mutation is present that would result in a T790M mutation in EGFR.

15. The method of claim 14, wherein the pair of primers includes at least one primer selected from among Seq ID Nos 4-7.

16. The method of claim 14, wherein the testing step further comprises the step of exposing the amplicons to a cleaving means, said cleaving means cleaves one but both not both of the wild type and mutant amplicons.

17. The method of claim 1, wherein the step of testing the sample comprises the steps of: performing PCR amplification using a pair of primers, and evaluating the amplicons to determine if a mutation is present that would result in a T790M mutation in EGFR, and wherein one of the primers used in the PCR amplification step binds at a position that includes the bases encoding a T790M mutation in EGFR.

18. The method of claim 17, wherein the primer that binds at a position including the bases encoding a T790M mutation in EGFR has a sequence such that the wild type genes and mutant genes are differentially amplified.

19. The method of claim 17, wherein the primer that binds at a position including the bases encoding a T790M mutation in EGFR is selected from among Seq ID Nos. 12-15.

20. The method of claim 1, wherein the step of testing comprises the steps of probing the sample with a probe oligonucleotide, wherein the probe binds preferentially to a 2369→T mutant or a wild type EGFR sequence, and detecting binding of the probe.

21. The method of claim 20, wherein the probe oligonucleotide is immobilized.

22. The method of claim 1, wherein the somatic gain-of-function mutation is a deletion from exon 19 of EGFR.

23. The method of claim 22, wherein the EGFR tyrosine kinase inhibitor is gefitinib or erlotinib.

24. A method for predicting development of acquired resistance to the therapeutic effects of a means for inhibiting epidermal growth factor (EGFR) tyrosine kinase in a patient that is suffering from a cancer, wherein the method comprises the steps of:
(a) obtaining a sample from the patient, wherein the cancer harbors a somatic gain-of-function mutation in the tyrosine kinase domain of EGFR that enhances the sensitivity of the cancer to the means for inhibiting EGFR tyrosine kinase,
(b) testing the sample to determine whether the gene encoding EGFR is present in a mutant form that encodes a T790M mutant of EGFR in addition to the somatic gain of function mutation, and
(c) identifying the cancer as one that has become or will become resistant to the means for inhibiting EGFR tyrosine kinase if the T790M mutant form is present or as having continuing sensitivity to the means for inhibiting EGFR tyrosine kinase if the T790M mutant form is absent,
wherein the testing of the sample in step (b) is performed by a method selected from the group consisting of:
(i) performing PCR amplification using a pair of primers that flank the region encoding amino acid 790 of EGFR to form amplicons that include the bases encoding amino acid 790 of EGFR, and evaluating the amplicons to determine if a mutation is present that would result in a T790M mutation in EGFR;
(ii) performing PCR amplification using a pair of primers, and evaluating the amplicons to determine if a mutation is present that would result in a T790M mutation in EGFR, and wherein one of the primers used in the PCR amplification step binds at a position that includes the bases encoding a T790M mutation in EGFR; and
(iii) probing the sample with a probe oligonucleotide, wherein the probe binds preferentially to a 2369C→T mutant or a wild type EGFR sequence, and detecting binding of the probe.

* * * * *

UNITED STATES PATENT AND TRADEMARK OFFICE
CERTIFICATE OF CORRECTION

PATENT NO.        : 8,501,413 B2                              Page 1 of 1
APPLICATION NO.   : 13/275161
DATED             : August 6, 2013
INVENTOR(S)       : Varmus et al.

It is certified that error appears in the above-identified patent and that said Letters Patent is hereby corrected as shown below:

In the Claims

Column 58, Claim 16, Line 50 should read-- ... said cleaving means cleaves one but not both ...

Signed and Sealed this
Twenty-fourth Day of December, 2013

Margaret A. Focarino
*Commissioner for Patents of the United States Patent and Trademark Office*